(12) United States Patent
Rouhani et al.

(10) Patent No.: US 6,262,265 B1
(45) Date of Patent: Jul. 17, 2001

(54) NON-HYDROLYZABLE ANALOGS OF HEROIN METABOLITES SUITABLE FOR USE IN IMMUNOASSAY

(75) Inventors: Riaz Rouhani, Concord, CA (US); Gerald F. Sigler, Carmel, IN (US)

(73) Assignee: Microgenics Corporation, Fremont, CA (US)

( * ) Notice: Subject to any disclaimer, the term of this patent is extended or adjusted under 35 U.S.C. 154(b) by 0 days.

(21) Appl. No.: 09/336,507

(22) Filed: Jun. 18, 1999

(51) Int. Cl.[7] ............... C07D 221/18; G01N 33/53; G01N 33/532
(52) U.S. Cl. ................. 546/44; 546/61; 546/69; 546/70; 546/74; 546/77; 546/106; 435/4; 435/6; 435/7; 435/7.21; 435/7.6; 435/7.9; 436/544; 436/545; 436/546; 530/300; 530/350; 530/387.1; 530/403
(58) Field of Search .............. 435/4, 6, 7, 7.21, 435/7.6, 7.9; 436/544, 545, 546; 530/300, 350, 387.1, 403; 546/61, 69, 70, 77, 44, 74, 106

(56) References Cited

U.S. PATENT DOCUMENTS

| | | | |
|---|---|---|---|
| 3,646,346 | 2/1972 | Catt | 250/83 |
| 3,817,837 | 6/1974 | Rubenstein et al. | 195/103.5 |
| 3,852,157 | 12/1974 | Rubenstein et al. | 195/63 |
| 3,996,345 | 12/1976 | Ullman et al. | 424/12 |
| 4,064,228 | 12/1977 | Gross | 424/1 |
| 4,161,515 | 7/1979 | Ullman | 424/8 |
| 4,208,479 | 6/1980 | Zuk et al. | 435/7 |
| 4,233,401 | 11/1980 | Yoshida et al. | 435/7 |
| 4,256,834 | 3/1981 | Zuk et al. | 435/7 |
| 4,261,968 | 4/1981 | Ullman et al. | 424/8 |
| 4,444,887 | 4/1984 | Hoffmann | 435/240 |
| 4,472,500 | 9/1984 | Milstein et al. | 435/68 |
| 4,491,632 | 1/1985 | Wands et al. | 435/240 |
| 4,551,426 | 11/1985 | Freytag et al. | 435/7 |
| 4,614,823 | 9/1986 | Kirkemo et al. | 544/300 |
| 4,708,929 | 11/1987 | Henderson | 435/7 |
| 5,032,503 | 7/1991 | Khanna et al. | 435/7.6 |
| 5,120,643 | 6/1992 | Ching et al. | 435/7.92 |
| 5,254,577 | 10/1993 | Carlson et al. | 514/376 |
| 5,254,677 | 10/1993 | Guder et al. | 435/7.9 |
| 5,334,538 | 8/1994 | Parker et al. | 436/525 |
| 5,439,798 | 8/1995 | Sigler et al. | 435/7.7 |
| 5,444,161 | 8/1995 | Manning et al. | 536/4.1 |
| 5,464,747 | 11/1995 | Eisenbeis et al. | 435/7.6 |
| 5,514,560 | 5/1996 | Manning et al. | 435/14 |
| 5,525,474 | 6/1996 | Sigler et al. | 435/7.7 |
| 5,763,196 | 6/1998 | Powell et al. | 435/7.6 |

FOREIGN PATENT DOCUMENTS

| | | | |
|---|---|---|---|
| 0 165 716 | 1/1990 | (EP) | G01N/534/33 |
| WO 90/02809 | 3/1990 | (WO) . | |
| WO 92/01047 | 1/1992 | (WO) . | |
| WO 93/20079 | 10/1993 | (WO) . | |
| WO 94/13804 | 6/1994 | (WO) . | |

Primary Examiner—Christopher L. Chin
Assistant Examiner—Lisa V. Cook
(74) Attorney, Agent, or Firm—Wood, Herron & Evans, LLP

(57) ABSTRACT

Novel chemical analogs are disclosed for the essential heroin metabolite 6-O-acetyl morphine (6MAM). The analogs optionally can be made to contain protein reactive groups, and can be used to form protein conjugates, fluorescently labeled compounds, and solid-phase adsorbants. The proteins conjugates can be used in turn to raise antibodies reactive with 6MAM and having a low cross-reactivity with the closely related opiates, morphine and codeine. The antibodies can be used in combination with labeled analogs in exquisitely sensitive immunoassays suitable for testing for heroin abuse.

15 Claims, 6 Drawing Sheets

MONOACETYLMORPHINE (MAM) ANALOG
6-O-ACETYL-

MONOACETYLMORPHINE (MAM) ANALOG
6-O-METHYLPHOSPHONYL-

MONOACETYLMORPHINE (MAM) ANALOG
6-O-DIMETHYLPHOSPHONYL-

MONOACETYLMORPHINE (MAM) ANALOG
6-O-CARBAMOYL-

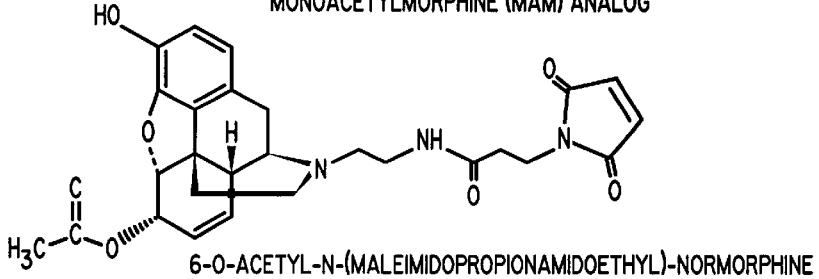

MAM ANALOG FOR PROTEIN CONJUGATION
MONOACETYLMORPHINE (MAM) ANALOG

6-O-ACETYL-N-(MALEIMIDOPROPIONAMIDOETHYL)-NORMORPHINE

FIG. 3A

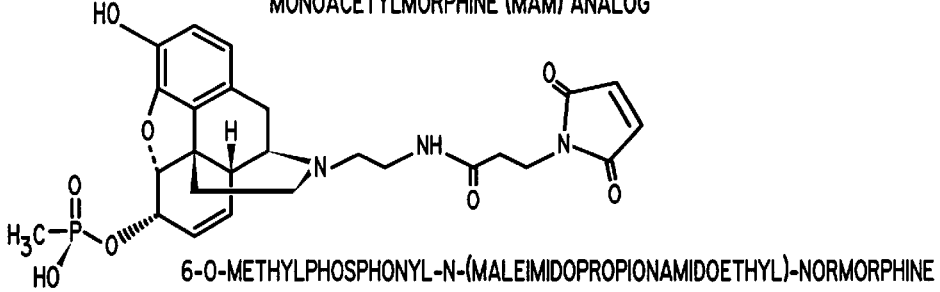

MAM ANALOG FOR PROTEIN CONJUGATION
MONOACETYLMORPHINE (MAM) ANALOG

6-O-METHYLPHOSPHONYL-N-(MALEIMIDOPROPIONAMIDOETHYL)-NORMORPHINE

FIG. 3B

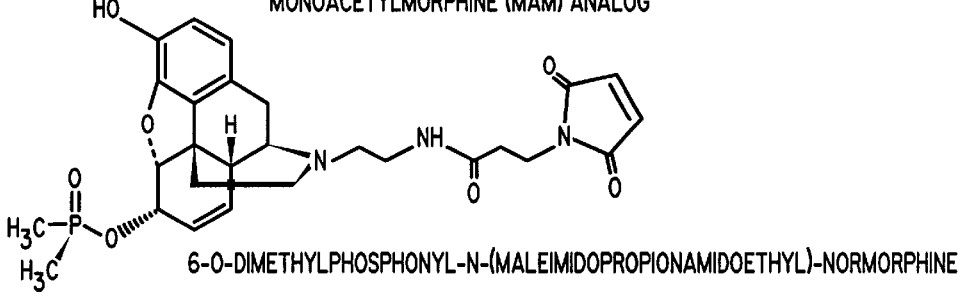

MAM ANALOG FOR PROTEIN CONJUGATION
MONOACETYLMORPHINE (MAM) ANALOG

6-O-DIMETHYLPHOSPHONYL-N-(MALEIMIDOPROPIONAMIDOETHYL)-NORMORPHINE

FIG. 3C

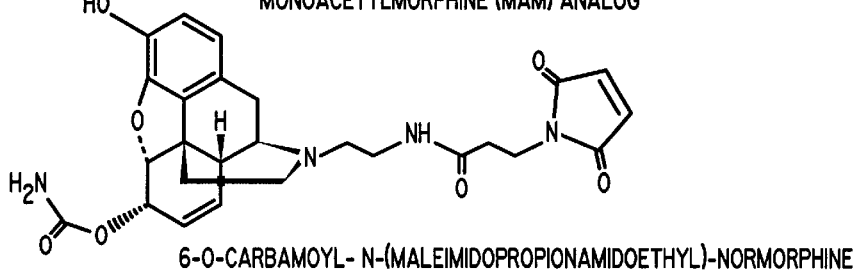

MAM ANALOG FOR PROTEIN CONJUGATION
MONOACETYLMORPHINE (MAM) ANALOG

6-O-CARBAMOYL- N-(MALEIMIDOPROPIONAMIDOETHYL)-NORMORPHINE

FIG. 3D

6-O-ACYTELMORPHINE

6-O-METHYLPHOSPHONYL-MORPHINE

6-O-DIMETHYLPHOSPHONYL-MORPHINE

6-O-CARBAMOYL-MORPHINE

NON-HYDROLYZABLE ANALOGS OF HEROIN METABOLITES SUITABLE FOR USE IN IMMUNOASSAY

TECHNICAL FIELD

This invention relates generally to the field of determining drug metabolites in biological samples. More specifically, it provides a system of analogs, conjugates and specific antibodies that can be used in assay systems for specific detection or quantitation of heroin abuse.

BACKGROUND

Testing for heroin abuse is complicated by the fact that heroin undergoes rapid metabolism to 6-O-acetyl-morphine (also known as 6-monoacetylmorphine, 6MAM). After an intramuscular administration of heroin, 6MAM appears in urine almost immediately. Levels of 6MAM remain positive in urine for about 8 hours, as detected by standard techniques such as GC/MS (Cone et al., Anal. Toxicol. 15:1, 1991). Heroin is then broken down into morphine, which is a metabolite of other opiates such as codeine.

A number of tests have been developed for measuring opiates in biological samples. Generally, immunoassays have been unsuccessful at discriminating between 6MAM and related compounds. Other opiate metabolites, such as morphine-3-glucuronide and morphine-6-glucuronide, may be present at levels approximately four to five orders of magnitude greater than 6MAM. Investigators have had to resort to more cumbersome and expensive techniques to determine the identity of an opiate in an unknown sample.

Solans et al. (J. Pharmaceut. Biomed. Anal. 8:905, 1990) determined various opiates in urine, including 6MAM, using GC-MS. Jenkens et al. (J. Anal. Toxicol 22:173, 1998) used GC-MS to detect 6MAM in postmortem cerebrospinal fluid. Bogusz et al. used chemical ionization-mass spectrometry-liquid chromatography to determine 6MAM and other morphine metabolites in samples collected from overdose victims on autopsy. Zuccaro et al. (J. Anal. Toxicol. 21:268, 1997) describe simultaneous determination of 6MAM, morphine glucuronides, and other opiates by liquid chromatography-atmospheric pressure ionspray-mass spectrometry.

Holt et al. (Anal. Chem. 68:1877, 1996) report a bioluminescent assay for heroin and its metabolites. The assay is based on heroin esterase, and morphine dehydrogenase, using bacterial luciferase from *Vibrio harveyi*. Heroin, morphine, and codeine are all detected.

International patent publication WO 93/20079 (Buechler et al.) report opiate derivatives and protein conjugates. In their synthetic compounds, the group at the 6-O-position is typically H—, $CH_3(CO)$—, or $CH_3CH_2$—. Some of the conjugates are proposed as immunogens, but the ability of the antibodies obtained to discriminate between opiates is not reported.

European patent application EP 0363041-A1 (Uda et al.) report monoclonal antibodies to morphine, made using a N-(4-bromobutyl) derivative. An immunoassay is reported using the antibody and a BSA normorphine conjugate. Cross-reactivity between morphine and each of cocaine, codeine, dihydrocodeine, ethylmorphine, fentanyl or methadone is reported as <1.0% or better, depending on the antibody tested.

U.S. Pat. No. 4,064,228 (Gross et al.) report antigens and immunoassays for morphine and related compounds. 3-Oxybenzomorphan derivatives are conjugated to immunogenic carriers using a linking site on an aryl group, and used to produce antibodies. The assays are reported as being primarily reactive with morphine, with an 11% cross-reactivity to codeine and a 7% cross-reactivity to monoacetylmorphine.

Fogerson et al. (J. Anal. Toxicol. 21:451, 1997) describe the qualitative detection of opiates such as heroin, 6MAM and morphine, in sweat. Immunoassay was conducted using an enzyme immunoassay kit from STC Technologies. Standardized to morphine, the assay also reacted with 6MAM (30% cross-reactivity), hydrocodone (143%), and codeine (588%). Discrimination between opiates was only possible using GC-MS. Similarly, the sweat testing by Kintz et al. (Clin Chem. 43:736, 1997) is done strictly by GC-MS.

Moeller et al. (Forensic Sci. Int. 70:125, 1995) report the detection of 6MAM in biological samples by GC/MS and radioimmunoassay. The radioimmunoassay used was obtained in kit form from Diagnostic Products Corporation. FIG. 4 of that article shows the reactivity of potential interfering substances in comparison with 6MAM. Based on 50% B/Bo points, cross-reactivity with heroin is ~50%, morphine ~30%, morphine-6-glucuronide ~20%. Reactivities with codeine are not titrated to the 50% point, but codeine and other interfering substances are clearly detectable.

Preferable to separation immunoassays (in which antibodies are used to capture the analyte) are homogeneous type assays, in which analyte-antibody complexes are detected in situ. A particularly powerful homogeneous assay system is the cloned enzyme donor immunoassay (CEDIA®), described in U.S. Pat. No. 4,708,929, and in Henderson, Clin. Chem. 32:1637, 1986. In a preferred form of the CEDIA® assay, two subunits of the enzyme beta-galactosidase associate to provide the detectable signal, which is quantitatively affected by analyte-specific antibody except in the presence of a sample containing free analyte.

Specific immunoassays of either type require the availability of an antibody that binds the analyte of interest but not potential interfering substances. An immunoassay for 6MAM capable of differentiating samples containing codeine or morphine requires an antibody with a very high relative affinity for 6MAM.

The limited specificity in current art 6MAM assays is attributable to the limited specificity in the antibody in the assay. This in turn is attributable to the unsuitability of current art immunogens for generating antibodies with a better ability to discriminate between the analyte and potential interfering substances.

DISCLOSURE OF THE INVENTION

The present invention provides a system for the improved detection of heroin metabolites in biological samples. New chemical analogs are provided for the metabolite 6-O-acetyl-morphine (also known as 6-monoacetylmorphine, 6MAM). These analogs are more stable than 6MAM, but have been found to mimic 6MAM in several important functional parameters. The hapten analogs can be used to construct immunogens, enzyme or enzyme donor conjugates, and other hapten conjugates.

The immunogens reproducibly generate antibodies with an exquisite ability to distinguish 6MAM in biological samples from morphine, codeine, and other potential interfering substances. The specific antibodies and the hapten conjugates can be used to distinguish and measure 6MAM in biological samples, such as those obtained from an individual suspected of substance abuse. Additional embodiments relate to certain reagents embodied in this invention, reagent combinations, and kits for performing an assay method for 6MAM in a biological sample.

In one embodiment, the invention encompasses 6MAM analog compounds having the following structure:

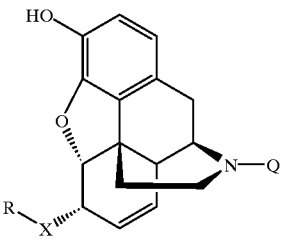

and its salts, wherein X is —O—, —S—, —NH— or —CH$_2$— and wherein R is selected from the group consisting of:

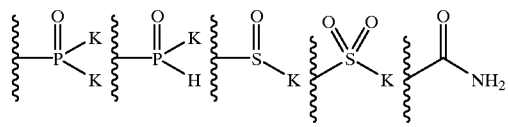

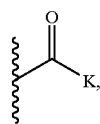

wherein K is —CH$_3$, —CF$_3$, —CHF$_2$, or —CH$_2$F; with the proviso that when R is

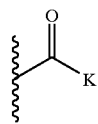

and K is —CH$_3$, X is not —O—; and

Q is —L$^1$—Z, where L$^1$ is a linker containing at least one carbon atom;

wherein Z is selected from the group consisting of the moieties

—NH$_2$,

—COOH,

—SH,

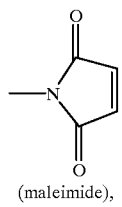

(maleimide),

—NH—C(=O)—L$^2$—M,

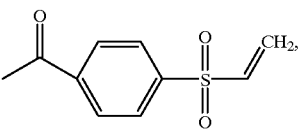

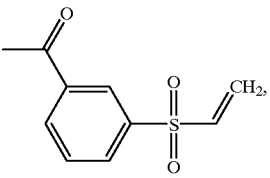

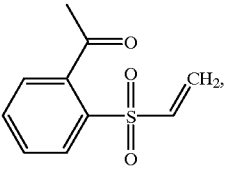

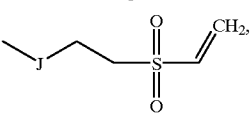

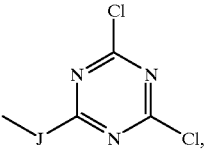

a moiety which reacts with a protein to form a covalent bond, or any combination or repetition of the aformentioned moieties;

where L$^2$ is a linker containing at least one carbon atom; where M is halide or maleimide; and wherein J is —O—, —S—, —NH— or —CH$_2$—. A preferred X group is —O—. Preferred R groups include

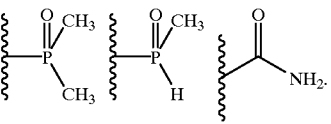

L$^1$ and L$^2$ are preferably independently selected from the group consisting of C$_1$–C$_{20}$ hydrocarbon chains, containing zero to ten heteroatoms selected from the group consisting of N, O, and S, and which contain at least as many carbon atoms as heteroatoms.

In certain embodiments, the compound is covalently attached to a label, either directly or through a linking group, to form a conjugate. The attachment can be anywhere on the molecule, including the normorphine nitrogen, and is preferably attached to the Z group of the compound. The label is preferably selected from a moiety containing a radioisotope, a fluorescent group, a fluorescence quenching group, a phosphorescent group, a chemiluminescent group, a chromophoric group, an electrochemically active group, an electrochemiluminescent group, a group that undergoes a change in fluorescence, phosphorescence, chemiluminescence or electrochemical property upon binding, a peptide, a protein, a protein fragment, an immunogenic carrier, an enzyme, an enzyme inhibitor, an enzyme substrate, an enzyme cofactor, an enzyme prosthetic group, an enzyme donor, a solid particle, a gold particle, an antibody, and a nucleic acid. The compound can also be attached to a solid surface or insoluble particulate.

In certain additional embodiments, the invention encompasses conjugates of the compounds where the compounds are derivatized by covalent attachment to a protein or peptide. The protein or peptide can be an enzyme, or an enzyme donor that complements with an enzyme acceptor to form an active enzyme complex. A preferred enzyme donor is ED28. In other embodiments, the protein or peptide can be immunogenic. The invention also encompasses methods of making these conjugates by conjugating the compound to the protein or peptide.

In another embodiment, the invention encompasses 6MAM analog compounds having the following structure:

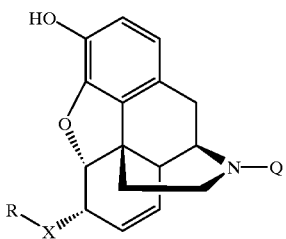

and its salts, wherein X is —O—, —S—, —NH— or —CH$_2$— and wherein R is selected from the group consisting of:

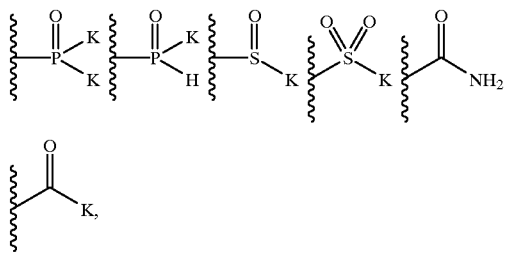

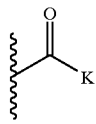

wherein K is —CH$_3$, —CF$_3$, —CHF$_2$, or —CH$_2$F; with the proviso that when R is

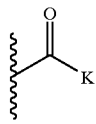

and K is —CH$_3$, X is not —O—; and

Q is —L$^1$—G, where L$^1$ is a linker containing at least one carbon atom, and G is selected from the group consisting of fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids.

In another embodiment, the invention encompasses 6MAM analog compounds having the following structure:

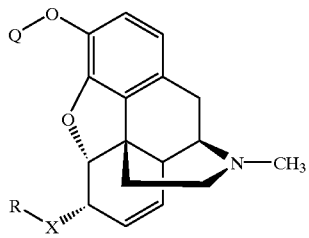

and its salts, wherein X is —O—, —S—, —NH— or —CH$_2$— and wherein R is selected from the group consisting of:

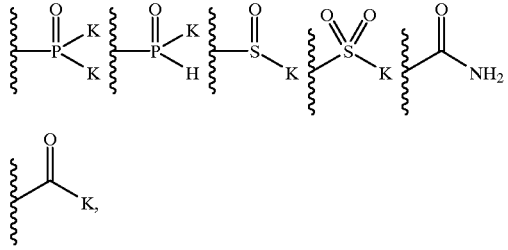

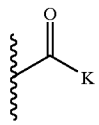

wherein K is —CH$_3$, —CF$_3$, —CHF$_2$, or —CH$_2$F; with the proviso that when R is

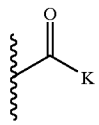

and K is —CH$_3$, X is not —O—;

Q is —L$^1$—Z, where L$^1$ is a linker containing at least one carbon atom;

wherein Z is selected from the group consisting of the moieties

—NH$_2$,

—COOH,

—SH,

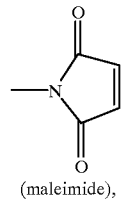

(maleimide),

—NH—C(=O)—L$^2$—M,

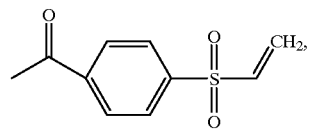

-continued

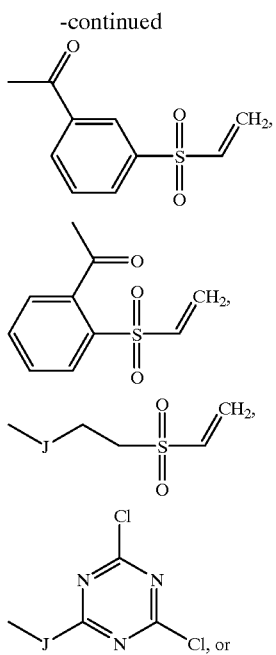

a moiety which reacts with a protein to form a covalent bond, or any combination or repetition of the aforementioned moieties;

where $L^2$ is a linker containing at least one carbon atom; and wherein J is —O—, —S—, —NH— or —CH$_2$—. In certain embodiments, these compounds are covalently attached to a label either directly or through a linking group. The label can be selected from the group consisting of a moiety containing a radioisotope, a fluorescent group, a fluorescence quenching group, a phosphorescent group, a chemiluminescent group, a chromophoric group, an electrochemically active group, an electrochemiluminescent group, a group that undergoes a change in fluorescence, phosphorescence, chemiluminescence or electrochemical property upon binding, a peptide, a protein, a protein fragment, an immunogenic carrier, an enzyme, an enzyme inhibitor, an enzyme substrate, an enzyme cofactor, an enzyme prosthetic group, an enzyme donor, a solid particle, a gold particle, an antibody, and a nucleic acid. The compounds can be covalently attached to a solid surface or insoluble particulate.

The invention also encompasses a method of obtaining an antibody specific for 6-O-acetyl morphine (6MAM), comprising immunizing an animal or contacting an immunocompetent cell or virus with a immunogenic 6MAM analog conjugate of this invention. The animal is preferably a vertebrate, more preferably a mammal. The antibodies may be in soluble form, or may be insolubilized by attachment to a solid surface, solid support, solid particle, or insoluble particle.

Yet another embodiment of the invention is an antibody specific for 6MAM, and having a cross-reactivity with potential interfering substances below a certain threshold. Preferred embodiments of the antibody have cross-reactivity with morphine, morphine 3-glucuronide, morphine 6-glucuronide, and codeine all less than about 10.0%. A yet more preferable embodiment is an antibody specific for 6MAM having a cross-reactivity with morphine, morphine 3-glucuronide and morphine 6-glucuronide all less than about 1.0%. Yet more preferable is an antibody specific for 6MAM having a cross-reactivity with codeine of less than about 1.0%. Another preferred embodiment is an antibody specific for 6MAM having a cross-reactivity with morphine of less than about 0.1%. Most preferred is an antibody specific for 6MAM having a cross-reactivity with codeine of less than about 1.0% and a cross-reactivity with morphine of less than about 0.1%.

Also embodied in the invention are reagent sets and reagent systems comprised of an antibody specific for 6MAM and labeled 6MAM analogs or 6MAM analog conjugates that can be used in combination to conduct an immunoassay for 6MAM. Thus, the invention also encompasses immunoassay reagents comprising a protein or peptide conjugate of a 6MAM analog of the invention, where the protein or peptide is an enzyme that undergoes a change in enzyme activity upon binding of the conjugate to an antibody specific for 6MAM; or the protein or peptide is an enzyme donor, where the ability of the enzyme donor to complement with an enzyme acceptor to form an active enzyme complex is affected by binding of the conjugate to an antibody specific for 6MAM.

Further embodiments of the invention include immunoassay methods for determining 6-O-acetyl morphine (6MAM) in a sample. One such method comprises the steps of combining the sample with an antibody specific for 6MAM under conditions that permit formation of a stable 6MAM-antibody complex and detecting or quantitating any 6MAM-antibody complex formed. Additional steps can include contacting the antibody with a labeled 6MAM or 6MAM analog under conditions that permit formation of a stable complex between the labeled compound and the antibody, separating any labeled compound not forming a stable complex, and measuring the complexed or separated label as a measure of 6MAM in the sample. Alternatively, the additional steps can include contacting the antibody with an enzyme or enzyme donor conjugate of a 6MAM analog under conditions that permit formation of a stable complex between the conjugate and the antibody; and measuring enzymatic activity or enzyme complementation as a measure of 6MAM in the sample. Both separation and homogeneous assay methods are included in the invention.

Further embodiments of the immunoassay methods of the invention are a method for determining 6-O-acetyl morphine (6MAM) in a sample by incubating a reagent mixture comprising the sample, an antibody specific for 6MAM, and a labeled 6MAM analog of the invention under conditions that permit formation of a stable complex between the antibody and any 6MAM in the sample, and detecting or quantitating fluorescence, phosphorescence, chemiluminescence, electrochemiluminescence, electrochemical property, or any change in these properties, as a measure of 6MAM in the sample. A 6MAM analog conjugated to an enzyme or enzyme donor can also be used in this method, with the mixture also comprising a substrate for the enzyme and, if an enzyme donor conjugate is used, an enzyme acceptor for the enzyme donor, where detecting or quantitating the enzymatic conversion of the substrate to a product is a measure of 6MAM in the sample. A preferable enzyme is beta-galactosidase; when an enzyme donor-enzyme acceptor combination is used, a preferred enzyme donor-enzyme acceptor complex is one that has beta-galactosidase activity.

The invention also encompasses a method for enriching 6MAM from a biological sample, comprising incubating the sample with an antibody specific for 6MAM under conditions that permit binding of the antibody to any 6MAM in the sample to form a complex, and separating complex that has formed from other components of the sample. The antibody may be bound to a solid support, solid surface, solid particle, or insoluble particle, in which case separation of the insolubilized antibody-6MAM complex is followed by washing the insolubilized complex, then by elution of the material bound to the antibody. After the solution has been enriched in 6MAM, it can be assayed for any 6MAM obtained.

BRIEF DESCRIPTION OF THE DRAWINGS

FIG. 3 is a series of chemical drawings showing 6MAM and three exemplary analogs adapted for protein conjugation with a protein-reactive group (maleimide) joined through a linking group to the normorphine nitrogen.

BEST MODE FOR CARRYING OUT THE INVENTION

The present invention is focused in part on the design and production of analogs for the heroin metabolite 6-acetylmorphine (6MAM), which can then be used for preparing immunogens and enzyme conjugates useful in immunoassays for the determination of 6MAM. The structure of 6MAM is shown below:

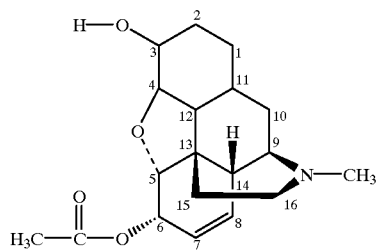

Figure 1:
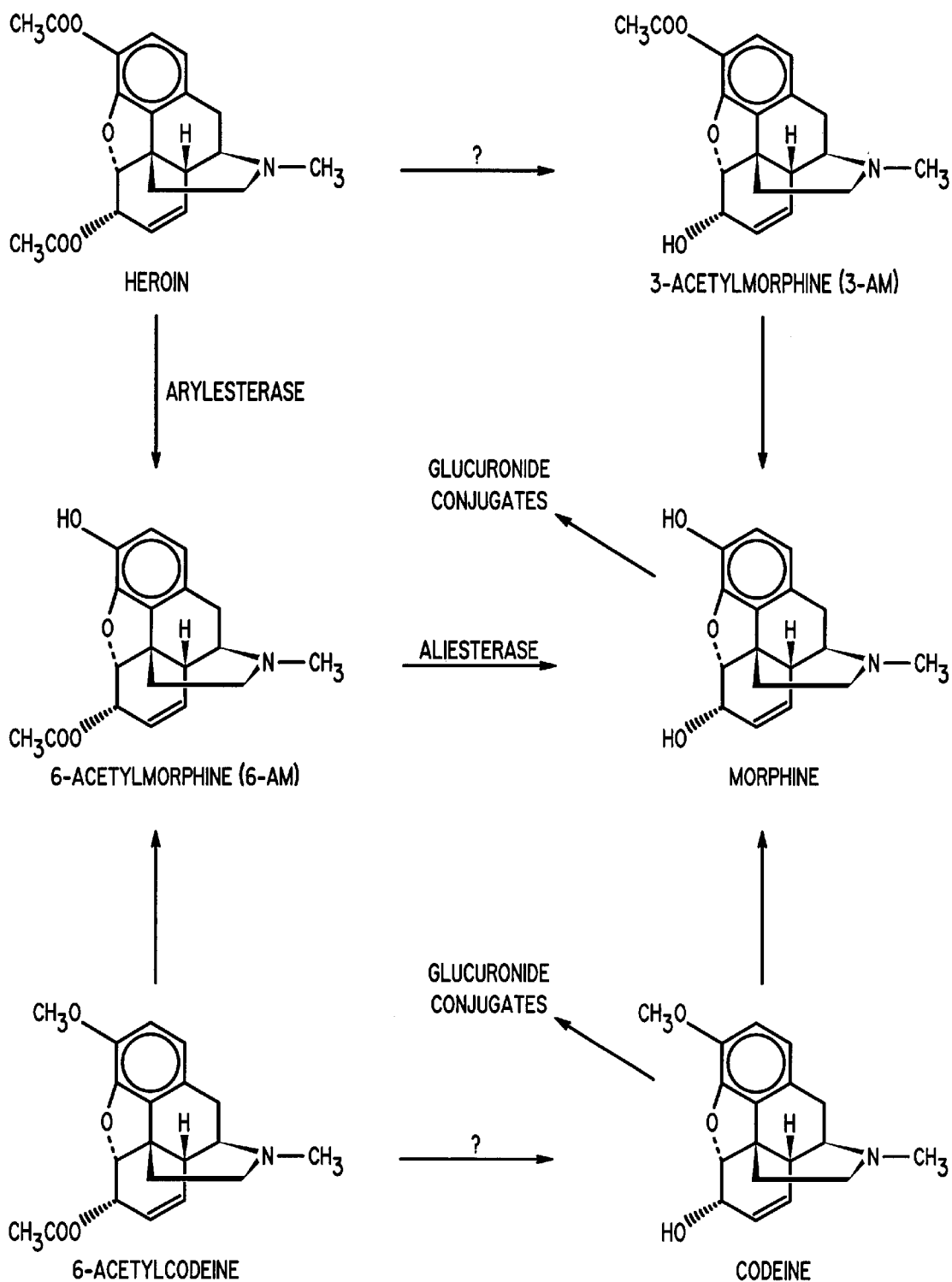
FIG. 1 is a chemical scheme showing metabolic pathways for opiates. Heroin is converted rapidly to the principle metabolite 6-acetyl morphine (6MAM) for which this disclosure provides methods of detection. Potential interfering substances include the closely related structures morphine, codeine, and their glucuronide conjugates.
Figure 2A:
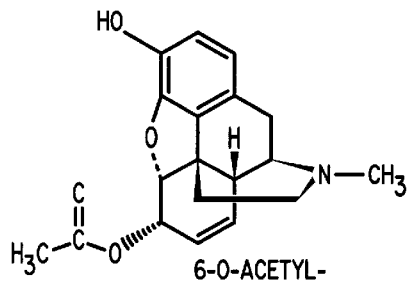
FIG. 2 is a series of chemical drawings comparing the structure of 6MAM (top structure) with exemplary analogs of this invention.
Figure 2B:
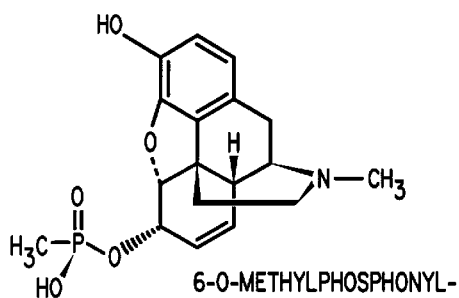
Figure 2C:
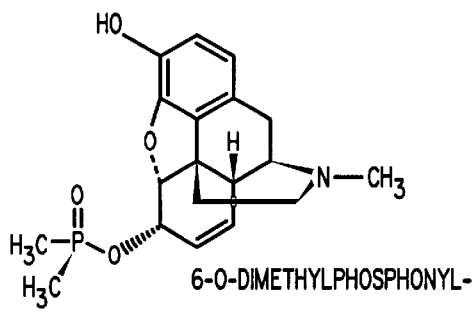
Figure 2D:
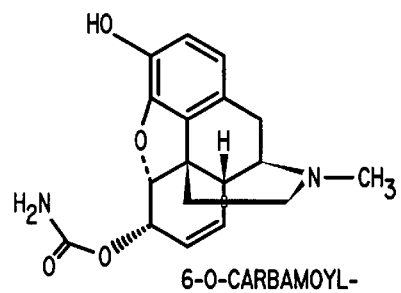

FIG. 1 shows the pathways for metabolism of opiates. Heroin is rapidly converted by the enzyme arylesterase to 6MAM. The 6MAM is further metabolized by aliesterase to morphine. Other opioid drugs, such as codeine, pholcodine, ethylmorphine (prescribed as an anti-tussive) are also metabolized to morphone (Pop et al., J. Chromatog. B661:245, 1994), and determination of morphine alone is not sufficient to distinguish heroin use from medically prescribed opiates. It would be advantageous to be able to test for 6MAM as evidence of heroin abuse, using a reagent system that did not cross-react with morphine, codeine, or their metabolites. Previously, antibodies able to distinguish between these compounds were not available.

Without limiting the invention to any particular theory of operation, it is a hypothesis of this invention that the difficulty in obtaining antibodies sufficiently specific for 6MAM is due in part to the hydrolytic and enzymatic lability of the 6-acetyl moiety in 6MAM. This invention overcomes this problem by supplying analog haptens in which the 6-acetyl moiety is replaced by chemical groups that mimic the acetyl group in spatial and/or electronic character, and are considerably more stable.

Analogs of 6MAM are prepared by replacing the 6-acetyl moiety with a carbamate, phosphonate, or sulfonate group. FIG. 2 compares the chemical structure of 6MAM (top structure) with the structures of exemplary analogs encompassed within this invention.

Figure 4A:
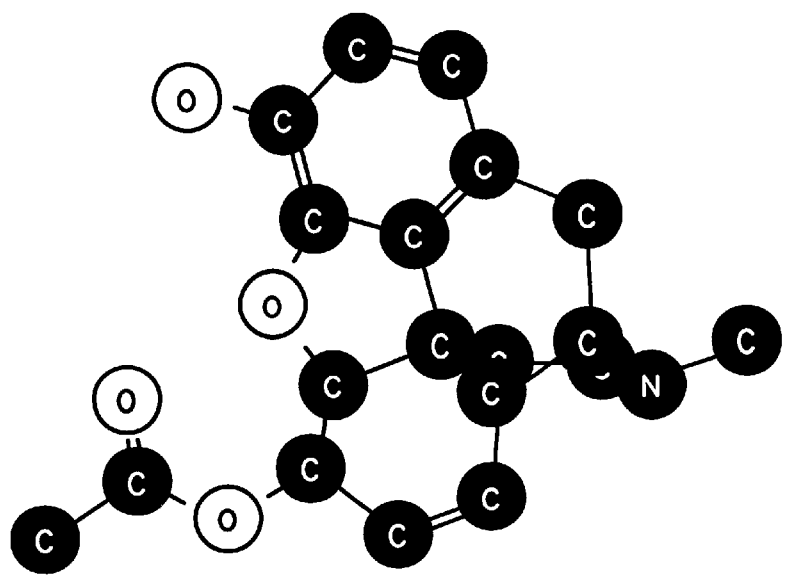
FIGS. 4(A), 4(B), 4(C) and 4(D) constitute a four-panel representation of 6MAM and exemplary 6MAM analogs of this invention in three-dimensions.
Figure 4B:
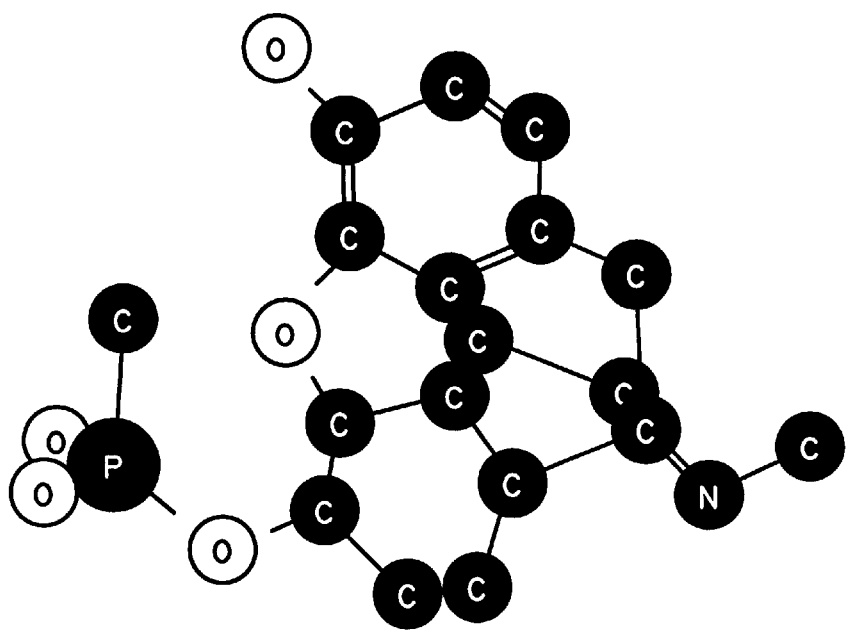
Figure 4C:
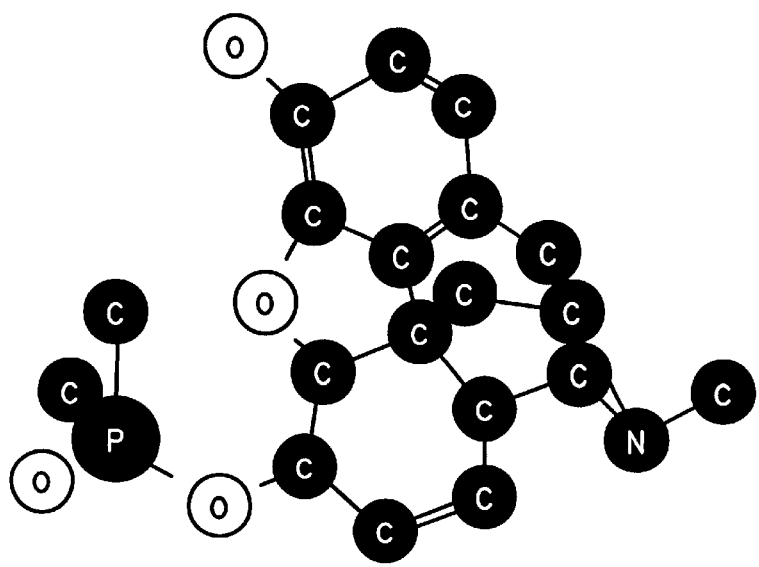
Figure 4D:
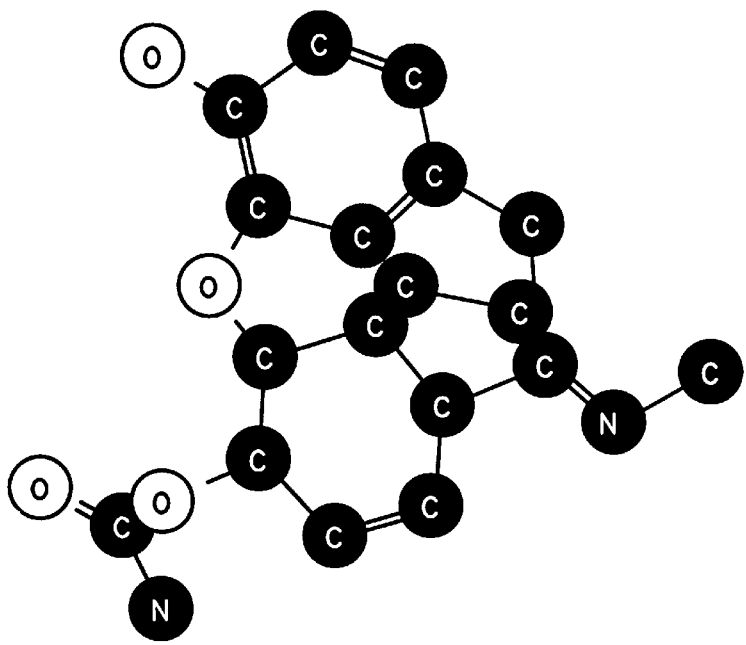

FIGS. 4(A) and 4(B) are three-dimensional representations of the exemplary analogs. It is hypothesized that the space occupied by the 6-acetyl group of MAM (top structure) is key to obtaining an antibody capable of distinguishing 6MAM from potential interfering substances. In the carbamoyl analog, the alpha methyl of the acetyl is replaced with the —$NH_2$ moiety of the carbamoyl group. In other analogs, the carbonyl carbon of the acetyl is replaced with phosphorus or sulfur. The oxygen attaching the group to the ring structure is present in several analogs, and is more resistant to cleavage in those analogs than in 6MAM.

The invention includes the analogs described above, as well as derivatives thereof that are not 6MAM. The analogs of this invention can either be used in the form shown, for example, as an internal standard or competitive binding compound in an assay system. They can also be adapted further. For example, they can be insolubilized by covalent attachment to a solid surface or insoluble particle, as described further on in this disclosure. Alternatively, they can be adapted for use in an assay system by covalently attaching a label, either directly, or through a covalent linking group. Suitable labels include radioisotopes such as $^{125}I$, a fluorescent group, a fluorescence quenching group, a phosphorescent group, a chemiluminescent group, an electrochemically active group, an electrochemiluminescent group, any group that undergoes a change in fluorescence, phosphorescence, chemiluminescence or electrochemical property upon binding, an enzyme or enzyme donor, an enzyme inhibitor, an enzyme substrate, an enzyme cofactor, and an enzyme prosthetic group. The analogs can be attached to latex particles for use in agglutination reactions; the latex particles can be opaque or contain a fluorophore or dye. The analogs can also be attached to colloidal gold. Examples of these assays are described in U.S. Pat. Nos. 5,120,643 and 5,334,538, and in Price and Newman, "Light Scattering Immunoassay," Principles and Practice of Immunoassay, (Price and Newman, eds.) New York: Stockton Press, 1991, pages 446–481.

Derivitization with aminomethylfluorescein is taught in U.S. Pat. No. 4,614,823. Enzyme and enzyme donors are described in the assay descriptions that follow. The analogs can also be adapted as immunogens by conjugating to an immunogenic substance, exemplified by proteins such as keyhole limpet hemocyanin (KLH).

"Poly(amino acids)", "proteins", "peptides", and "polypeptides" are terms used interchangeably herein to describe polymers of amino acids of any sequence, typically at least 5 amino acids in length, linked by peptide bonds. Of particular interest are proteins that can be used as immunogenic carriers, and proteins that provide a detectable signal for assay purposes, particularly enzymes and enzyme donor polypeptides.

Conjugates between 6MAM analogs and any type of protein or peptide, such as an enzyme, enzyme fragment, or immunogenic protein, can be prepared using any suitable linking chemistry. The reader is referred generally to Hermanson, G. T., "Bioconjugate Techniques", Academic Press: New York, 1996; and "Chemistry of Protein Conjugation and Cross-linking" by S. S. Wong, CRC Press, 1993.

It is convenient to attach proteins and other substituents by way of the nitrogen in the normorphine ring. A functional spacer can be introduced, which will allow accessibility to the analog once conjugated. Exemplary are protein reactive groups of the structure —$L^1$—Z, where $L^1$ is a linker containing at least one carbon atom, and is preferably a $C_1$–$C_{20}$ hydrocarbon chain containing zero to ten heteroatoms selected from the group consisting of N, O, and S, and which contains at least as many carbon atoms as heteroatoms;

and Z is selected from the group consisting of:

—$NH_2$
—COOH
—SH

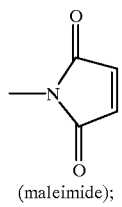
(maleimide);

—NH—C(=O)—$L^2$—M;

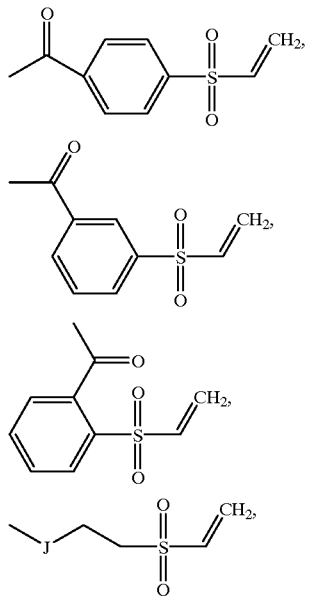

or

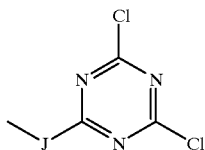

where $L^2$ is a linker containing at least one carbon atom, and is preferably a $C_1$–$C_{20}$ hydrocarbon chain containing zero to ten heteroatoms selected from the group consisting of N, O, and S, and contains at least as many carbon atoms as heteroatoms; where M is halide or maleimide; and wherein J is S, O, or N.

The phrase "a linker containing at least one carbon atom" is meant to refer to any generic linking group between two other groups, e.g., a linker between hapten and protein, or a linker between hapten and a functional group suitable for attachment to another molecule, which contains at least one carbon atom. The linker group is preferably a $C_1$–$C_{20}$ hydrocarbon chain containing zero to ten heteroatoms selected from the group consisting of N, O, and S, and which contains at least as many carbon atoms as heteroatoms. Examples of such generic linking groups include, but are not limited to, —O—$(CH_2CH_2O)_n$—, where n is an integer between 1 and 10 (i.e., a polyethylene glycol linker); —$CH_2CH_2$—phenyl—$CH_2CH_2$— (in ortho, meta, or para connection); —$CH_2CH_2$—CONH—$CH_2CH_2$— (i.e., an amide linkage), —C(=O)—CHS—NH— (i.e., an amino acid linker, where S is a naturally or non-naturally occurring amino acid side chain) or indeed, any straight-chain, branched, cyclic, or combination of straight-chain, branched, or cyclic linking group that will serve as a covalent linkage between the two other groups. Preferred linkers are $C_1$–$C_{20}$ alkyl groups.

FIG. 3 illustrates the structures of some exemplary analogs of this invention derivatized with a protein reactive group. The functional linker is an ethyl group, and the protein-reactive group is a maleimide, all attached to the normorphine nitrogen. This permits the acetyl group (in the case of 6MAM) or the phosphonyl or carbamoyl group (in the case of the analogs) to be accessible at the other end of the molecule for antibody binding.

One method of preparing such compounds is as follows. Normorphine is first alkylated at the nitrogen to introduce a functional spacer. Preferred functional spacer groups are aminoalkyl or carboxyalkyl groups where the alkyl group is $(CH_2)_n$, with n=1–20. The alkylation is typically accomplished by reacting normorphine with an N-protected haloalkylamine or a carboxyl-protected haloalkylcarboxylic acid. The halide leaving group can be Cl, Br, or I (preferably Br or I). The N-protection or carboxyl protecting groups are chosen to be removable under conditions which do not affect the normorphine portion of the molecule. Preferred N-protecting groups are urethanes such as t-butyloxycarbonyl (BOC) and benzyloxycarbonyl (Z), which are removed by acidolysis and the phthalimido protecting group which is removed by hydrazinolysis. Preferred carboxyl protecting groups are the t-butyl ester which is removed by acidolysis or hydrogenolysis or methyl/ethyl esters which are removed by saponification. A particularly preferred alkylating reagent is N-BOC-2-bromoethylamine. Alkylation is typically accomplished by reaction in an alcohol or a dipolar aprotic solvent, such as dimethylformamide (DMF) or dimethylsulfoxide (DMSO). The reaction is performed in the presence of an inorganic base, such as sodium bicarbonate or sodium carbonate. Alternatively, an organic tertiary amine can be employed as base such as triethylamine or diisopropylethylamine. Depending upon the reactivity of the alkylating reagent and the solvent system employed, the reaction may be heated. In a preferred example, N-BOC-2-bromoethylamine is reacted with normorphine in DMF with sodium bicarbonate as base and a temperature from 25° C. to 100° C., preferably 50° C. to 70° C., for at least 1 h, preferably 12–24 h.

In a second step, the 3-phenolic OH of normorphine is selectively protected in the presence of the free 6-OH group. Typical protecting groups include acyl esters such as acetyl or benzoyl. Ethers such as benzyl, t-butyl, or alkoxymethyl may also be used. Preferred protecting groups are methoxyethoxymethyl (MEM) or methoxymethyl (MOM) ethers which are introduced under mild conditions and readily removed by mild acidolysis. In a particularly preferred example, the 3-phenolic OH of N-BOC-amino alkyl normorphine is selectively reacted with methoxyethoxymethyl chloride (MEM-Cl) in a chlorinated solvent such as dichloromethane in the presence of a tertiary amine such as diisopropylethylamine. The reaction is performed at a temperature of −30° C. for 1–24 hr, preferably 5–25° C. for 2–8 hr. The resultant intermediate N-BOC-aminoalkyl 3-O-MEM-normorphine is ready for modification of the 6-OH group to generate 6-acetylmorphine hapten analogs.

For synthesis of a 6-carbamate analog, the N-BOC-aminoalkyl-3-O-MEM-normorphine is first reacted with a phosgene equivalent, disuccinimidyl carbonate in a chlorinated solvent such as dichloromethane containing an organic base such as triethylamine to give an intermediate succinimidyl-mixed carbonate. The mixed carbonate is further reacted with ammonia to give the desired 6-carbamyl derivative. Finally, both the MEM and BOC protecting groups are removed simultaneously by acidolysis to give the hapten analog, N-aminoalkyl-6-O-carbamyl-normorphine. The hapten analog may be directly conjugated to carrier proteins for immunogen or labels via the amino function using any of the procedures well known in the art of bioconjugate chemistry. In one non-limiting example, the amine is acylated with a maleimidoalkyl N-hydroxysuccinimide ester linker to obtain an activated hapten analog which is reactive towards thiol groups on carrier proteins, enzymes, enzyme fragments or other labels.

For synthesis of a 6-phosphonyl analog, a phosphonyl halide, preferably dimethylphosphonyl chloride, is first reacted at 0–30° C., preferably 0–5° C., with a heterocyclic amine such as tetrazole, triazole or imidazole, preferably tetrazole, in a polar solvent such as pyridine or collidine. The resultant phosphonyl tetrazolide, triazolide, or imidazolide is then reacted with N-BOC-aminoalkyl-3-O-MEM-normorphine at 0–30° C. to give the 6-phosphonylated analog. The protecting groups are removed by acidolysis to give the N-aminoalkyl-6-O-phosphonyl analog. As with the 6-O-carbamyl analog, direct conjugation or further extension with reactive linkers may be performed at this stage.

Analog-protein conjugates are typically prepared by synthesizing the analog with a protein-reactive group, incubating the modified analog with the protein under conditions that permit the conjugation reaction to occur, and then separating out the conjugate. For example, a protein conjugate can be prepared by combining an excess of a maleimide adduct with a protein having free thiol groups. Free sulfhydryls may be provided in the form of free cysteine residues or by reducing protein disulfide bonds by a reagent such as dithiothreitol. Alternatively, thiol groups can be added to a protein having free primary amino groups by reacting with 2-iminothiolane (IT) in aqueous buffer, followed by removal of unreacted IT. A detailed protocol for the thiolation of the protein KLH is provided in U.S. Pat. No. 5,439,798.

For the purposes of obtaining specific antibodies against 6MAM, an 6MAM analog-protein conjugate of this invention will comprise a plurality of 6MAM analogs covalently bonded to an immunogenic protein carrier selected for its ability to provide a general immunostimulatory effect. Various protein carriers may be employed, including serum albumin, serum globulins, ocular lens proteins, lipoproteins, ovalbumin, thyroxine binding globulin, and synthetic polypeptides. KLH is especially preferred.

The term "antibody" as used in this disclosure refers to both polyclonal and monoclonal antibodies and related antigen recognition units. The ambit of the term deliberately encompasses not only intact immunoglobulin molecules, but also such fragments and derivatives of immunoglobulin molecules as may be prepared by techniques known in the art, and retaining the antibody activity of an intact immunoglobulin. In this context, "antibody activity" refers to the ability of an antibody to bind a specific antigen in preference to other potential antigens via the antigen combining site located within a variable region of an immunoglobulin. Fragments and other derivatives of immunoglobulins can be prepared by methods of standard protein chemistry, such as subjecting the antibody to cleavage with a proteolytic enzyme like pepsin, papain, or trypsin; and reducing disulfide bonds with such reagents as dithiothreitol. Genetically engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

For general techniques used in raising, purifying and modifying antibodies, and the design and execution of immunoassays, the reader is referred to *Handbook of Experimental Immunology* (D. M. Weir & C. C. Blackwell, eds.); *Current Protocols in Immunology* (J. E. Coligan et al., eds., 1991); David Wild, ed., *The Immunoassay Handbook* (Stockton Press N.Y., 1994); and R. Masseyeff, W. H. Albert, and N. A. Staines, eds., *Methods of Immunological Analysis* (Weinheim: VCH Verlags gesellschaft mbH, 1993).

Polyclonal antibodies of this invention are raised by administration of the immunogenic 6MAM analog-protein conjugate to an animal host, usually mixed with an adjuvant. Any animal host which produces antibodies can be used. The animal is preferably a vertebrate, more preferably a mammal. The immunogen is conveniently prepared for injection by rehydrating lyophilized immunogen to form a solution or suspension. Preferred adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of 6MAM antibody using an 6MAM-protein conjugate or other 6MAM analog in a standard immunoassay or precipitation reaction.

Polyclonal antisera will typically contain antibodies not reactive with 6MAM and anti-6MAM antibodies cross-reactive with other substances including morphine. Methods for purifying specific antibodies from a polyclonal antiserum are known in the art. A particularly effective method is affinity purification using a column of 6MAM conjugated to a solid phase. One manner of preparing an 6MAM column is to conjugate 6MAM or an analog of this invention to a protein other than the protein used in the immunogen, and then attach the conjugate to a commercially available activated resin, such as CNBr-activated SEPHAROSE™. The anti-6MAM is passed over the column, the column is washed, and the antibody is eluted with a mild denaturing buffer such as 0.1 M glycine, 0.2 M NaCl, pH 2.5.

Monoclonal antibodies of this invention can be prepared by a number of different techniques known in the art. For hybridoma technology, the reader is referred generally to Harrow & Lane (1988), U.S. Pat. Nos. 4,491,632, 4,472,500, and 4,444,887, and Methods in Enzymology, 73B:3 (1981). The most common way to produce monoclonal antibodies is to immortalize and clone a splenocyte or other antibody-producing cell recovered from an animal that has been immunized against 6MAM as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing is performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Alternative methods for obtaining monoclonal antibodies involve contacting an immunocompetent cell or viral particle with an analog-protein complex of this invention in vitro. In this context, "immunocompetent" means that the cell or particle is capable of expressing an antibody specific for the antigen without further genetic rearrangement, and can be selected from a cell mixture by presentation of the antigen. Immunocompetent eukaryotic cells can be harvested from an immunized mammalian donor, or they can be harvested from an unimmunized donor and prestimulated in vitro by culturing in the presence of immunogen and immunostimulatory growth factors. Cells of the desired specificity can be selected by contacting with the immunogen under culture conditions that result in proliferation of specific clones but not non-specific clones. Immunocompetent phage may be constructed to express immunoglobulin variable region segments on their surface. See Marks et al., New Engl. J. Med. 335:730, 1996; WO patent applications 94/13804, 92/01047, 90/02809; and McGuinness et al., Nature Biotechnol. 14:1149, 1996. Phage of the desired specificity may be selected, for example, by adherence to an 6MAM-protein complex attached to a solid phase, and then amplified in E. coli.

Antibodies obtained using any of the aforementioned techniques are screened or purified not only for their ability to react with 6MAM, but for a low cross-reactivity with potential interfering substances. "Cross reactivity" is determined in a quantitative immunoassay by establishing a standard curve using known dilutions of the target analyte, 6MAM. The standard curve is then used to calculate the apparent concentration of the interfering substance present in various known amounts in samples assayed under similar condition. The cross reactivity is the apparent concentration divided by the actual concentration multiplied by 100. The preferred immunoassay for determining cross-reactivity is a CEDIA® type assay using an ED28-6MAM donor polypeptide, described in detail in Example 10. Alternatively, the cross-reactivity can be determined in the same type of immunoassay in which the antibody will ultimately be used.

It is generally worth screening antibodies for cross reactivity with other pharmaceutical compounds that subjects may be taking collaterally, particularly those eliminated in urine and having a polycyclic structure with some resemblance to 6MAM. Levels of cross-reactivity for interfering compounds of this nature are generally less than 10%, and with increasing preference, less than 5%, 1%, 0.1% or 0.01 %. Of especial concern are morphine, morphine metabolites such as morphine 3-glucuronide and morphine 6-glucuronide. Also of especial concern is codeine and its metabolites, such as codeine 6-glucuronide. Lower cross-reactivities for these related substances, either alone or in combination, are increasingly more preferred.

Antibodies to 6MAM according to this invention are useful for detection of 6MAM and for purifying 6MAM from a mixture Purification of 6MAM using antibody in immunoaffinity techniques is useful in isolating preparative amounts of 6MAM from contaminants that copurify by other techniques. Purification of 6MAM from clinical samples in trace amounts is desirable where the samples potentially contain a substance that is not 6MAM but may complicate readings in the detection system. For example, GC/MS tests generally require extraction of analyte from the aqueous sample. Standard liquid or solid phase extraction can give high background signals and poor sensitivity of detection. Analyte-specific immunoadsorption improves the extent of selection and also concentrates the analyte into a smaller volume than the original sample.

Potential methods of immunoaffinity purification include double antibody precipitation, protein A precipitation, and the formation of other types of antibody conjugates. A preferred method is solid phase adsorption. The antibody is attached to any suitable resin, the original sample is contacted with the resin, the resin is washed, and the sample is eluted. Preferred resins include: Sepharose® (Pharmacia), Poros® resins (Roche Molecular Biochemicals, Indianapolis), Actigel Superflow™ resins (Sterogene Bio-separations Inc., Carlsbad Calif.), and Dynabeads™ (Dynal Inc., Lake Success, N.Y.).

A preferred coupling procedure is as follows: The required amount of activated Sepharose® was weighed, taking into account the desired coupling ratio and the fact that 1 g freeze-dried material swells to 3.5 mL gel volume. The gel is reconstituted and washed in wash buffer (1 mM HCl) (3 mL and then 200 mL per gram), and then washed in coupling buffer (0.1 M NaHCO$_3$, 0.5 M NaCl, pH 8.3) (50 mL per gram) using a Buchner funnel. The antibody is dissolved or exchanged into coupling buffer, and 5–10 mg are coupled per mL. The gel cake is transferred to a suitably sized container, the antibody is added, and the volume is adjusted to make a 50% slurry. The suspension is mixed end-over-end for 2 h at room temperature, or overnight at 2 to 8° C. (Stirring is avoided to prevent shearing of the beads.) The proportion of antibody successfully coupled is determined by measuring A$_{280}$ before and after coupling. Blocking buffer is then added (1 M ethanolamine pH 8.0, or 0.2 M Tris buffer, pH 8.0), and the suspension is mixed end-over-end for a further 2 h at room temperature, or overnight at 2 to 8° C. The gel is washed in a Buchner funnel with coupling buffer, second wash buffer (0.1 M Acetate, 0.5

M NaCl, pH 4.0), and then coupling buffer (100 mL each per gram). The affinity resin can then be diluted with prepared inactivated Sepharose® 4B to yield the desired binding capacity.

Resins of this kind are typically preserved in refrigerated conditions or in the presence of a preservative such as 0.1% sodium azide. Separation may be conducted by column chromatography or batch elution. In a typical separation procedure, 10 mL of a sample being tested for the presence of 6MAM (such as a urine sample from a human subject) is combined with 200 μL of a 50% slurry of the anti-6MAM resin. The reaction and extraction can be conveniently carried out in a conical sample container with a 10 mL capped reservoir fitted at the bottom with a frit and a plugged tip. A small amount of buffer may also be added to the sample if the antibody is sensitive to pH variation between samples. The mixture is then capped and the resin is kept suspended for about 30 to 120 min on a platform rocking mixer or rotator. The resin is separated from the sample (for example, by filtration or centrifugation), and washed with 10 ml, of phosphate-buffered saline, and then twice with water. After the final wash, the resin is sucked dry by applying a vacuum for 2–5 seconds. 1 mL methanol is then added, the resin is incubated for ~2–5 min, and the methanol is recovered. The methanol eluate can then be characterized for the presence of 6MAM, which correlates with the presence of 6MAM in the original sample. Successful elution can be confirmed by running parallel extractions on samples containing standard amounts of 6MAM, or by including an internal standard in the sample, such as a cross-reactive substance or a stable isotope-labeled internal standard. 6MAM analogs suitable for this purpose are described earlier in this disclosure.

Embodied in this invention are immunoassay methods for the presence of 6MAM in a sample of interest, including but not limited to bodily fluids from subjects suspected of being administered heroin, particularly bodily fluids from humans. Suitable samples include biological samples taken from subjects, optionally diluted or modified to facilitate the assay, experimental samples generated by any chemical or biological method, and standards containing known concentrations of 6MAM or other substances used for assay calibration.

Liquid biological samples of particular interest are urine, serum, plasma, and fluids taken during autopsy (such as cerebrospinal fluid). Tissue samples can be extracted into liquid medium for immunoassay. Hair samples can also be tested by extracting into a liquid medium. For example, hair can be washed in air and acetone to remove oils, dried, and then pulverized in a ball mill. 20–30 mg powdered hair are then incubated in a neutral buffer for about 5 h at 40° C. Also suitable are postmortem cerebrospinal fluid or vitreous humor. Sweat samples can be obtained using, for example, a PharmChek sweat patch (Sudormed, Santa Ana, Calif.), comprising a semi-occlusive dressing consisting of a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) Fogerson et al., J. Anal. Toxicol. 21: 451, 1997, or with acetonitrile.

In most instances, the assays will involve using an antibody raised against an 6MAM analog-protein conjugate of this invention or having the characteristics of such an antibody, particularly a low cross-reactivity with morphine or codeine.

The procedure entails combining the sample with the antibody under conditions that permit the formation of a stable complex between the substance to be tested (described herein as the "analyte", and typically 6MAM), and the antibody. This is followed by detecting any 6MAM-antibody complex that is formed. A "stable complex" is a complex between antibody and analyte (typically non-covalently associated) that persists at least as long as it takes the presence of the complex to be measured by the intended method.

Assays of this invention include both qualitative and quantitative assays. Typical quantitative methods involve mixing the analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise stated, the act of "measuring" or "determining" in this disclosure refers alternately to qualitative and quantitative determination.

Assays of this invention include both separation-based and homogeneous assays. In separation based assays, the detecting of the complex involves a process wherein the complex formed is physically separated from either unreacted analyte, unreacted antibody, or both. See, e.g., U.S. Pat. No. 3,646,346. The complex may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled analog or antibody to facilitate detection or quantitation of the complex. Suitable labels are radioisotopes such as $^{125}I$, enzymes such as peroxidase and beta-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

In homogeneous assays, the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents (U.S. Pat. Nos. 3,996,345, 4,161,515, 4,256,834, and 4,261, 968); enzyme and enzyme inhibitor pairs on different reagents (U.S. Pat. Nos. 4,208,479, 4,233,401, 3,817,837 and European patent EP 165716); latex turbidometric inhibition assays (Price and Newman, "Light Scattering Immunoassay," Principles and Practice of Immunoassay, (Price and Newman, eds.) New York: Stockton Press, 1991, pages 446–481) and chromophore and cliromophore modifier pairs on different reagents (U.S. Pat. No. 4,208,479). A preferred homogeneous assay system is the cloned enzyme donor immunoassay, described in more detail below.

As used in this disclosure, a "6MAM analog" refers to a compound that is able to compete with 6MAM for binding to the antibody being used in the assay. Useful labels for use in the analogs of this invention for immunoassay techniques include but are not limited to radioisotopes, a fluorescent group, a fluorescence quenching group, a phosphorescent group, a chemiluminescent group, an electrochemically active group, an electrochemiluminescent group, any group that undergoes a change in fluorescence, phosphorescence, chemiluminescence or electrochemical property upon binding, an enzyme, an enzyme donor, an enzyme inhibitor, an enzyme substrate, an enzyme cofactor, and an enzyme prosthetic group.

Assays of this invention include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with an analog of the analyte for binding to another reagent, such as an antibody. CEDIA® is an example of a competition assay. The invention also embodies assays that are neither sandwich nor competition assays, as in certain assays involving immunoprecipitation.

Immunoassays specific for 6MAM using anti-6MAM antibodies of this invention are rendered specific by virtue of the specificity of the antibody. For assays further employing protein conjugates, such as when a hapten (i.e., 6MAM or a 6MAM analog) is labeled with an enzyme polypeptide, the hapten can be attached to the protein conjugate by any suitable method. In certain preferred embodiments, the chemistry described herein for formation of immunogenic protein conjugates of 6MAM analogs is also used to prepare the protein conjugate used as an assay reagent. In this way, the hapten core is presented to the antibody in about the same orientation as during the immunization event when the antibody was generated.

Assay methods of this invention include homogeneous enzyme assays in which 6MAM or an analog is conjugated to an active enzyme. The conjugation is arranged so that the binding of an anti-6MAM antibody to the analog affects enzymatic activity in a quantitative fashion. If a sample containing 6MAM is premixed with the antibody, the antibody will complex with the 6MAM and be prevented from binding to the enzyme conjugate. In this way, the activity of the enzyme can be correlated with the amount of 6MAM present in the sample. Enzyme amplification assays and the conjugation of opiates to enzymes is reported in U.S. Pat. No. 3,852,157.

Enzyme complementation assays are generally described in U.S. Pat. No. 4,708,929. Related reagents and methods are taught in U.S. Pat. Nos. 5,254,577; 5,444,161; 5,464,747; and 5,514,560. Cloned enzyme donor immunoassays for procainamide and N-acetytlprocainamide (NAPA) are described in U.S. Pat. Nos. 5,439,798 and 5,525,474. For the purposes of patent prosecution in the U.S., the aforelisted patents are hereby incorporated herein in their entirety. Enzyme complementation assays based on the enzyme beta-galactosidase are available commercially under the registered trademark CEDIA®. The reader is referred to CEDIA® product inserts and technical manuals for further information.

Typically, an enzyme complementation immunoassay of this invention involves combining the sample with: an 6MAM-specific antibody; an enzyme donor polypeptide conjugate; an enzyme acceptor polypeptide (wherein the enzyme acceptor polypeptide is capable of forming with said enzyme donor polypeptide conjugate an active enzyme complex in the absence of an antibody to 6MAM), and a substrate capable of being transformed by the active enzyme complex into a product. The amount of product is then measured, usually as a function of time.

For complementation assay purposes, the 6MAM-specific antibody is preferably an antibody raised against an analog-protein conjugate of this invention, or having the characteristics of such an antibody, especially a low level of cross-reactivity with morphine, morphine-3-glucuronide, morphine-6-glucuronide, and codeine. Besides being screened for cross reactivity, desirable antibodies have three other features. One, referred to as "inhibition", relates to how well the antibody binds the enzyme-donor conjugate and blocks formation of active beta-galactosidase. Sufficient inhibition (preferably at least about 70%) is needed in order to provide an adequate signal. A second criterion is the titer of the antibody required to obtain the desired level of inhibition. Inhibition at lower antibody levels is preferred. A third criterion, referred to as "modulation", relates to how well the sample analyte is able to compete with the conjugate for enzyme binding. Modulation is calculated as the difference in enzyme rate between a sample having a given analyte concentration and a sample having no analyte, divided by the rate at the given analyte concentration. Better modulation at the target concentration for the positive/negative decision point (the assay "cut-off"), preferably 10 ng/mL in the case of 6MAM, correlates with better assay sensitivity and precision at concentrations near the cut-off. Antibodies have been obtained that fit these criteria well, and have the designations 2G5, 2E1, 13A9, 3F4, 2A11 and 8C10.

The enzyme-donor enzyme-acceptor pair is a pair of polypeptides which spontaneously assemble in reagent buffer to form an active enzyme complex. The active enzyme complex is capable of enzymatically transforming a substrate into a product that is differentially detectable. Typically, the product is a different color from the substrate and can be quantified in a spectrophotometer. The donor and acceptor pair are typically two functional subunits of a common enzyme. The subunits may be noncovalently associated in the native enzyme, or they may be defective versions of a common polypeptide that complement each other when together.

Preferred enzyme-donor and enzyme-acceptor polypeptides are based on the enzyme beta-galactosidase polypeptide. A "beta-galactosidase polypeptide" is a polypeptide identifiable on the basis of its amino acid sequence or enzymatic activity as being developed from an enzyme with beta-galactosidase activity. The definition encompasses not only naturally occurring beta-galactosidase, but also fragments, deletion mutants, fusion proteins, mutants, and other variants based thereupon obtained by such processes as enzymatic fragmentation and genetic engineering of relevant encoding sequences. Particular beta-galactosidase polypeptides are described in the aforelisted U.S. Patent applications pertaining to cloned enzyme donor immunoassays.

Beta-galactosidase enzyme acceptors are preferably produced by a deletion mutant of the beta-galactosidase gene. EA22, one of the preferred acceptors, has a deletion of amino acid residues 13–40. Other enzyme acceptor fragments of beta-galactosidase which contain the natural sequence which includes amino acid position 602 may also be used. Other examples include EA5, EA 11, EA14, EA17, EA18, EA20, EA23 and EA24. The distal end of the deleted segment normally falls between amino acid positions 26 and 54 of the beta-galactosidase sequence. In EA22, the distal end of the deletion segment is amino acid 40.

A particularly preferred beta-galactosidase enzyme donor is ED28. ED28 is a 90 amino acid peptide containing residues 6–45 of beta-galactosidase, with cysteines at positions 1 and 46 (relative to the numbering of the original beta-galactosidase fragment). The sequence of ED28 is (SEQ ID NO:1) Met-Asp-Pro-Ser-Gly-Asn-Pro-Tyr-Gly-Ile-Asp-Pro-Thr-Gln-Ser-Ser-Pro-Gly-Asn-Ile-Asp-Pro-Cys-Ala-Ser-Ser-Asn-Ser-Leu-Ala-Val-Val-Leu-Gln-Arg-Arg-Asp-Trp-Glu-Asn-Pro-Gly-Val-Thr-Gln-Leu-Asn-Arg-Leu-Ala-Ala-His-Pro-Pro-Phe-Ala- Ser-Trp-Arg-Asn-Ser-Glu-Glu-Ala-Arg-Thr-Asp-Cys-Pro-Ser-Gln-Gln-Leu-Ala-Gln-Pro-Glu-Trp-Gly-Leu-Glu-Ser-Arg-Ser-Ala-Gly-Met-Pro-Leu-Glu; see also European Patent Application No. 90308937.3 and U.S. Pat. Nos. 4,708,929, 5,444,161, and 5,763,196. The two cysteine residues can be used for exact and reproducible placement of sulfhydryl-reactive adducts of 6MAM or 6MAM analogs as described earlier. Before conjugation with the hapten, reducing reagent that is generally used in the storage of ED28 is removed by a suitable desalting technique, such as on a Pharmacia NAP5™ column as described in U.S. Pat. No. 5,439,798. The 6MAM or 6MAM analog is then conjugated with the maleimide adducts as described elsewhere in this disclosure. Adjustment of the linkage can be performed by monitoring enzyme inhibition by an 6MAM-specific antibody. Typical linker groups used are maleimide adducts, where the maleimide nitrogen and the 6MAM or 6MAM analog, nitrogen are linked by —(CH$_2$CH$_2$)—.

Preferred substrates for use in immunoassays based on beta-galactosidase include those described in U.S. Pat. Nos. 5,032,503; 5,254,677; 5,444,161; and 5,514,560. Amongst the preferred substrates is chlorophenolred-beta-D-galactopyranoside. Optimization of other features and conditions of the assays embodied by this invention is a matter of routine experimentation within the skill of the ordinary artisan.

Reagents and buffers used in the assays of this invention can be packaged separately or in combination into kit form to facilitate distribution. The reagents are provided in suitable containers, and typically provided in a package along with written instructions relating to assay procedures.

The analogs of 6MAM and the specific antibodies of this invention can be insolubilized by attachment to a solid phase. This can be, for example, a vessel wall, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Suitable particulate materials include agarose, polystyrene, cellulose, polyacrylamide, latex particles, magnetic particles, and fixed red cells. Suitable commercially available matrices include Sepharose® (Pharmacia), Poros® resins (Roche Molecular Biochemicals, Indianapolis), Actigel Superflow™ resins (Sterogene Bioseparations Inc., Carlsbad, Calif. , and Dynabeads™ (Dynal Inc., Lake Success, N.Y). The choice is not critical, and will generally depend on such features as stability, capacity, accessibility of the coupled antibody, flow rate (or the ability to disperse the resin in the reaction mixture), and ease of separation.

Suitable approaches for attaching the substance on to the solid surface will depend on the nature of the analog or antibody, and the solid phase. Attachment systems include those shown in the following table:

TABLE 1

| Conjugation Chemistry | | |
|---|---|---|
| Site of Attachment or Derivitization on Resin | Reagent Used | Site of Attachment of Antibody |
| Hydroxyl groups | CNBr | Amino groups |
| Hydroxyl groups | Carbonyldiimidazole | Amino groups |
| Aldehyde groups | NaBH$_4$ or NaCNBH$_3$ | Amino groups |
| Sulfhydryl-reactive group (RCH$_2$I, R-maleimide, disulfide) | (Spontaneous) | Disulfide Bonds (after reduction) |
| Amino groups | Water-soluble carbodiimides | Carboxyl groups |
| Carboxyl groups | Water-soluble carbodiimides | Amino groups |
| N-hydroxysuccinimide esters | (Spontaneous) | Amino groups |
| Epoxide groups | (Spontaneous) | Amino groups |
| Hydrazide groups | (Spontaneous) | Carbohydrate groups (after periodate oxidation) |
| Protein A or Protein G | (Spontaneous) | Antibody Fc region |

For example, antibodies purified by chromatography on Protein A affinity chromatography can be attached to cyanogen bromide-activated Sepharose® CL-4B (Pharmacia, Piscataway, N.J.) as recommended by the manufacturer. The resin is prepared to contain approximately 0.8 mg of bound antibody per mL of resin bed volume. The procedure can be conducted as follows: The required amount of activated Sepharose® is weighed, taking into account that 1 g freeze-dried material swells to 3.5 mL gel volume. The gel is reconstituted and washed in wash buffer (1 mM HCl) (3 cycles of resin wash, at 200 mL per gram), and then washed three times with coupling buffer (0.1 M NaHCO$_3$, 0.5 M NaCl, pH 8.3) (50 mL per gram) using a Buchner funnel. The antibody is dissolved or exchanged into coupling buffer, and 5–10 mg are coupled per mL. The gel cake is transferred to a suitably sized container, the antibody is added, and the volume is adjusted to make a 50% slurry. The suspension is mixed end-over-end for 2 h at room temperature, or overnight at 2 to 8° C. (Stirring is avoided to prevent shearing of the beads.) The proportion of antibody successfully coupled can be determined by measuring A$_{280}$ before and after coupling. Blocking buffer is then added (1 M ethanolamine pH 8.0, or 0.2 M Tris buffer, pH 8.0), and the suspension was mixed end-over-end for a further 2 h at room temperature, or overnight at 2 to 8° C. The gel is washed in a Buchner funnel with coupling buffer, second wash buffer (0.1 M Acetate, 0.5 M NaCl, pH 4.0), and then coupling buffer (100 mL each per gram). After final wash with coupling buffer, the resin is made into a 50% (v/v) slurry with phosphate-buffered saline (PBS, pH 7.4, 0.09% sodium azide). The prepared affinity resin can be optionally diluted with a 50% (v/v) slurry of inactivated Sepharose® 4B to yield the desired binding capacity.

Of course, antibodies for insolubilization can be selected according to different criteria than the ones used for assay purposes. Modulation is not important, but high capacity (or affinity) and low cross reactivity with potential interfering substances, such as morphine and codeine, is desirable for a solid-phase antibody. An antibody specific for 6MAM and suitable for use as an insolubilized antibody has been obtained and has the laboratory designation 3F4.

Insolubilized antigen can be used in assays for antibody, and insolubilized antibody can be used in assays for immunogen. Labeling methods and principles of various types of immunoassay are provided earlier in this disclosure. In a solid phase assay, the test sample is typically mixed with the solid phase to permit binding of any test substance. Then the solid phase is separated from the sample and any unbound material, and the solid phase is washed. The next step is to determine on the solid phase any substance that has bound from the sample. This can be done by including in the reaction mixture a labeled equivalent of the analyte or antibody being tested for, and determining the amount of analyte or antibody by competition. One such method is described in U.S. Pat. No. 4,551,426. Alternatively, the solid phase can be used in a sandwich format, reacting the washed resin with a detecting agent capable of determining any substance which has bound the resin specifically.

Insolubilized antigen and antibody can also be used as affinity resins for the purpose of purifying or enriching substances that bind them. The method comprises incubating the insolubilized antigen or antibody with the source material under conditions permitting the substance to bind, removing the source material, optionally washing the solid phase, and then recovering the bound substance. Materials that bind by way of antigen-antibody reactivity can generally be eluted using organic solvents, high or low pH buffers (such as dilute acetic acid, or glycine buffer, pH 2.4), high salt (such as a buffered solution of 1 M KSCN), or organic solvents (such as methanol).

In a variation of this, insolubilized antigen or antibody can be used to pre-process a sample before testing in an assay system. For example, if a sample tests positive for 6MAM, it can be treated with an appropriate amount of anti-6MAM resin and then retested. The test result will be confirmed as positive, if the resin succeeds in removing detectable analyte from the resin. Further elaboration of the adsorption method of running a confirmatory test is described in International Patent application WO 98/26644.

In another variation, the resin is used not to eliminate the analyte from the sample, but to enrich for it. A preferred system constitutes a sample extraction kit in the ImmunElute™ product line by Microgenics. An antibody to 6MAM with the desired specificity characteristics is coupled to agarose as already described. The resin is provided as a 5 mL suspension (50% vol/vol) in a suitable buffer containing 0.1% sodium azide as preservative. The kit also contains poly prep columns of 10 mL each, having top caps and removal plugs on the bottom outlet below the frit or filter holding the resin in place.

To perform the affinity enrichment, the biological sample is clarified if necessary to remove turbidity, by centrifugation or filtration. Negative control and standards are prepared by providing analyte-free urine, dividing into separate test tubes, and adding known amounts of analyte over the expected range. The control, standards, and test samples (volumes up to ~10 mL) are then layered onto a corresponding extraction column. If appropriate and desired, an internal control can be included in each sample, as long as the controlling substance is also recognized by the antibody and does not interfere with either the extraction or the assay. Certain analogs of 6MAM according to this invention qualify for this purpose. The resin is mixed to provide an even suspension, and 200 µL suspension is added to each sample column. The columns are then capped and mixed on a rocking mixer for 30 to 120 min, then placed on a suitable rack, small-end down. The plug is removed and the column is allowed to drain. The resin is washed (e.g., 10 mL phosphate-buffered saline, followed by 2 times 10 mL deionized and distilled water. After drying the resin under a light vacuum, the sample is then eluted. To accomplish this, the column is replugged. 10 mL of a suitable eluting solvent such as methanol is pipetted onto the column, and allowed to stand for 2–5 min. The plug is then removed and the methanol is eluted from the bottom of the column. The methanol extract can then be tested by a suitable method, such as GC/MS. Alternatively, an aliquot can be diluted in aqueous buffer and tested by immunoassay.

Additional illustration of the development and use of reagents and assays according to this invention are provided in the Example section below. The examples are provided as a further guide to a practitioner of ordinary skill in the art, and are not meant to be limiting in any way.

EXAMPLES

Example 1

Preparation of N-tert-butyloxycarbonyl-2-bromoethylamine

N-BOC-bromoethylamine was prepared as follows. 2-Bromoethylamine hydrobromide (6.15 g, 30 mmol) was dissolved in a mixture of 30 mL each water and dioxane and the solution was chilled in an ice bath to 0–5° C. Separately, a solution of 3.27 g (15 mmol) di-tert-butyl-dicarbonate in 35 mL dioxane was prepared. Finally a solution of 1 N sodium hydroxide (30 mL), was prepared. Dropwise addition of the di-tert-butyl-dicarbonate and the 1 N sodium hydroxide solutions to the stirred 2-bromoethylamine hydrobromide solution was begun at 0–5° C. The di-tert-butyl-dicarbonate addition took place over 30 min, and the 1N sodium hydroxide addition was complete after 15 min.

The ice bath was then removed and the reaction was stirred for 2 h at room temperature. After a total of 2.5 h reaction time, the mixture was diluted with 100 mL dichloromethane and transferred to a separatory funnel. The biphasic mixture was separated and the upper aqueous phase was added back to the separatory funnel and washed with 50 mL dichloromethane. The phases were separated and the dichloromethane wash was added to the original dichloromethane phase. The combined dichloromethane extract was washed twice with 50 mL of 5% w/v citric acid solution followed by two washes with 50 mL of 10% w/v sodium chloride solution. The washed dichloromethane extract was collected, dried over 5 g magnesium sulfate, filtered and rotary evaporated to give 3.22 g (95% yield) of a clear liquid product.

$^1$H-NMR (CDCl3): 1.47 ppm (9, s, BOC), 3.4–3.6 ppm (4, m+m, CH2—CH2), 5.00 ppm (1, br s, NH).

Example 2

N-(N'-BOC-2-aminoethyl)-normorphine

N-(N'-BOC-2-aminoethyl)-normorphine was prepared as follows: Normorphine (202.5 mg, 0.747 mmol), was dissolved in 5 mL of dry dimethylformamide (DMF) and added to a round bottom flask and reflux condenser under argon. Finely pulverized sodium bicarbonate (316 mg, 3.76 mmol) was added and the suspension was heated to 54° C. with stirring. In the meantime, a solution of N-BOC-bromoethylamine (0.83 g, 3.69 mmol) in 1 mL dry DMF was prepared to give 1.6 mL of solution. A 400 µL aliquot of the latter solution was added to stirred normorphine solution. The temperature of the reaction was increased to 60–62° C. After 2 h and 5 h reaction time, additional 400 µL aliquots of N-BOC-bromoethylamine solution were added to the reaction. The reaction was then stirred overnight at 60–62° C. Finally, the remaining 400 µL of N-BOC-bromoethylamine solution was added to the reaction mixture and the mixture was stirred for 3 additional h at 60–62° C. (total reaction time 24 h).

The reaction mixture was rotary evaporated at 30° C. to give an oily residue. The residue was dissolved in a mixture of 20 mL chloroform and 10 mL water. The phases were separated and the upper aqueous phase was reextracted with 10 mL chloroform. The chloroform layers were combined and washed with 10 mL water followed by 10 mL 10% w/v sodium chloride solution. The chloroform layer was collected, dried over 1.6 g magnesium sulfate, filtered and rotary evaporated to give 264 mg of crude product as a foam. The crude product was purified by silica gel flash chromatography in a 1.5×25 cm column eluted with chloroform/methanol (9/1 v/v). Fractions containing product were located by TLC spot testing for UV-absorbing material followed by TLC in chloroform/methanol (9:1) on UV+ fractions. Pure fractions were pooled and rotary evaporated to give 195.4 mg of product as a tan foam (63% yield).

$^1$H-NMR (CDCl3): 1.5 ppm (s, BOC), 4.2 ppm (1 H, m, H6), 4.9 ppm (d, H5), 5.1 ppm (br s, NH), 5.3 ppm (1 H, d, H8), 6.5 & 6.65 (2 H, d of d, H1 & H2).

Example 3

3-O-methoxyethoxymethyl-N-(N'-BOC-2-aminoethyl)-Normorphine

3-O-MEM-N-(N'-BOC-aminoethyl)-normorphine was prepared as follows: N-(N'-BOC-aminoethyl)-normorphine (253.7 mg, 0.61 mmol) was dissolved in 4 mL dichloromethane under argon. The solution was treated with 110 μL (0.63 micromole) diisopropylethylamine then chilled in an ice bath to 0–5° C. Methoxyethoxymethyl-chloride (MEM-Cl), 73 μL (0.64 mmol) was then added and the reaction mixture was stirred at 0–5° C. for 1.5 h The ice bath was removed and the reaction was stirred for 2.5 additional h at room temperature.

The reaction mixture was worked up by diluting with 10 mL dichloromethane, transferring to a separatory funnel and washing twice with 10 mL of water followed by 8 mL of 10% w/v sodium chloride solution. The dichloromethane solution was dried over 0.75 g magnesium sulfate, filtered, and rotary evaporated to give crude product as an oil. The crude product was purified by silica gel flash chromatography in a 1.5×26 cm column eluting with chloroform/methanol (9:1). Fractions containing product were located by TLC spot testing for UV absorbing material followed by TLC in chloroform/methanol (9:1) of UV+ fractions. Pure fractions were pooled and rotary evaporated to give 211.1 mg of product as a gum (68% yield).

$^1$H-NMR (CDCl3): 1.5 ppm (s, BOC CH3s), 3.35 ppm (s, MEM CH3O), 3.5 & 3.8 ppm (ms, MEM O—CH2—CH2—O), 5.2 ppm (d, H8), 5.1 & 5.55 ppm (ds, MEM O—CH2—O), 5.7 ppm (d, H7), 6.5 & 6.8 ppm (d of d, H1& H2).

Example 4

3-O-MEM-6-O-Carbamoyl-N-(N'-BOC-2-aminoethyl)-normorphine

The title compound was prepared as follows: 3-O-MEM-N-(N'-BOC-aminoethyl)-normorphine, 23.7 mg (47 micromole), was dissolved in 2 mL dichloromethane under argon. Disuccinimidyl-carbonate (DSC), 36 mg (141 micromole) was added followed by triethylamine, 20 μL (141 micromole). The reaction was stirred at room temperature. The progress of the reaction was monitored by UV on a 10×0.46 cm reverse phase C18 column (Vydac 90 Å pharmaceutical) eluting with a 20–40% linear gradient of acetonitrile in 0.1% v/v TFA/water (flow=1 mL/min; slope=1%/minute).

After 2 h, an additional 26 mg (101 micromole) of DSC and 13 μL (93 micromole) triethylamine were added. Reaction was continued for a total of 26 h at room temperature. At this time nearly all the starting material eluting with a k'=5.9 was converted into a presumed 6-O-succinimidyl-carbonate intermediate product eluting with a k'=10. At this time 1 mL of dioxane was added followed by 1 mL of 0.5 M ammonia in dioxane. After 5 min, HPLC indicated nearly complete conversion to 6-O-carbamate product eluting with a k'=6.9. The solution was rotary evaporated to dryness and the residue of crude product was redissolved in 2 mL acetonitrile. The crude product was purified in two runs by preparative HPLC on a 2.2×25 cm C18-HPLC column (Vydac 300 Å) in the same gradient system as used in the analytical runs and the flow rate of 16 mL/min. Major peak fractions from 2 runs were pooled and lyophilized to give 9.8 mg of product which was immediately deprotected (see example 5).

Example 5

6-O-Carbamoyl-N-(2-aminoethyl)-normorphine bistrifluoroacetate

The title compound was prepared as follows: 3-O-MEM-6-O-Carbamoyl-N-(N'-BOC-2-aminoethyl)-Normorphine, 9.8 mg (17.9 micromole) was treated with 4 mL of 50% v/v trifluoroacetic acid (TFA) in dichloromethane for 1.5 h at room temperature. The reaction was rotary evaporated to give an oil. Diethyl ether was added to the oil to obtain a solid. Filtration and drying gave 5.3 mg of product.

$^1$H-NMR (D2O): 2.1–2.5 ppm (2 H, ms, H15), 4.3 ppm (1H, m, H9), 5.1–5.3 ppm (2 H, ms, H5 & H6), 5.55 ppm (1H, d, H8), 5.8 ppm (1H, d, H7); 5.65–5.85 (2H, d of d, H1 & H2); no BOC or MEM resonances.

Example 6

6-O-Carbamoyl-N-(3-maleimido-propionamidoethyl)-Normorphine

6-O-Carbamoyl-N-(MPAE)-Normorphine was prepared as follows: 6-O-Carbamoyl-N-(2-aminoethyl)-Normorphine bisTFA salt, 11.7 mg (19.9 micromole) was dissolved in 0.5 mL DMF under argon. Triethylamine, 3.5 μL (25.1 micromole) was added followed by 6.7 mg (25.2 micromole) maleimidopropionic acid N-hydroxysuccinimide ester (MPS). The reaction was monitored by C18-HPLC on a 0.46×10 cm column (Vydac 90 Å Pharmaceutical) using a linear gradient of 5–25% acetonitrile in 0.1% v/v TFA/water at 1 mL/min (slope=1%/min). After 20 min, nearly all of the starting material (k'=1.9) was converted to product eluting at k'=9.4. Preparative HPLC on a 2.2×25 cm C18 HPLC column (Vydac 300 Å) in the same gradient at a flow rate of 16 mL/min gave 4.98 mg of purified product (49% yield).

$^1$H-NMR(D2O): 2.1–2.5 ppm (2 H, ms, H15), 2.55 ppm (2 H, t, MPAE CH2CO), 3.85 ppm (2 H, t, MPAE CH2-N), 4.3 ppm (1 H, m, H9), 5.15 ppm (1 H, m, H6), 5.25 ppm (1 H, d, H5), 5.55 ppm (1 H, d, H8), 5.8 ppm (1 H, d, H7), 6.7 & 6.8 ppm (2 H, d of d, H1&2), 6.9 ppm (2 H, s, maleimide H); Electrospray MS: expected MW=508.5; measured MW=508.5; UV: max=286 nm.

Example 7

3-O-MEM-6-O-Dimethylphosphinyl-N-(N'-BOC-2-aminoethyl)-Normorphine

The title compound was prepared as follows: Dimethylphosphinyl chloride, 28.5 mg (0.253 mmol) was dissolved in 0.5 mL anhydrous pyridine under argon and chilled to 0–5° C. in an ice bath. Separately, 1H-tetrazole, 23.5 mg (0.336 mmol) was dissolved in 0.5 mL pyridine and the solution was added to the chilled dimethylphosphinyl chloride solution and stirred for 9 min. Finally a solution of 3-O-MEM-6-O-N-(N'-BOC-2-aminoethyl)-Normorphine, 59.8 mg (0.118 mmol) in 1 mL of pyridine was prepared and added to the dimethylphosphinyl chloride/tetrazole mixture at 0–5° C. After stirring an additional 10 min. at 0–5° C., the ice bath was removed and the reaction was stirred at room temp.

The reaction was monitored by C18-HPLC on a 0.46×10 cm column (Vydac 90 Å Pharmaceutical) in a linear gradient of 10–60% acetonitrile in 20 mM triethylamine acetate (pH 6.0) at 1.0 mL/min (slope=1%/min). Starting material eluting with a k'=9.6 was converted to product eluting with a k'=9.8. Reaction was nearly complete after 70 min. at room temperature. After 2 h., the reaction mixture was rotary evaporated at 30° C. to give an oil. The oil was redissolved in chloroform, 15 mL, and water, 10 mL. The biphasic solution was separated and the lower chloroform phase was washed with 10 mL water followed by 10 mL 10% w/v sodium chloride solution. The chloroform phase was dried over 1 g magnesium sulfate, filtered and rotary evaporated to crude product as an oil.

The crude product was redissolved in 250 $\mu$L of chloroform and purified on a 20×20 preparative TLC plate (Whatman PK6F) in chloroform/methanol (9:1) mobile phase. The plate was developed for 10 cm then removed from the TLC tank and air dried. Two major bands for product ($R_f$ 0.40) and starting material ($R_f$ 0.55) were visualized under a UV lamp. The product band was cut from the plate and eluted on a filter with 3×10 mL mobile phase. The eluate was rotary evaporated to give 41.3 mg of purified product as an oil (60% yield).

$^1$H-NMR (CDCl3): 1.5 ppm ( 9 H, s, BOC CH3s), 1.55 & 1.70 ppm (6 H, d of d, P—CH3s), 2.1–2.5 ppm (2 H, ms, H15), 3.4 ppm (s, MEM CH3O), 3.55 & 3.85 (4 H, ts, MEM O—CH2—CH2—O), 5.25 ppm (2H, d of d, MEM-O—CH2—O), 5.35 & 5.55 ppm (2 H, ds, H7 & H8), 6.5 & 6.85 ppm (2 H, ds, H1 & H2).

Example 8

6-O-Dimethylphosphinyl-N-(2-aminoethyl)-Normorphine bisTFA salt

The title compound was prepared as follows. The purified 3-O-MEM-6-O-Dimethylphosphonyl-N-(N'-2-BOC-aminoethyl)-Normorphine, 41.3 mg (71 micromole) was dissolved in 2 mL dichloromethane and treated with 2 mL TFA. The reaction was stirred at room temperature under argon for 105 min. monitoring the HPLC in the system described in example 7. All of the starting material eluting with k'=9.8 was converted to a product eluting at k'=3.75. After 105 min. the reaction mixture was rotary evaporated to an oil. Addition of diethyl ether, 5 mL, gave a gummy solid which was converted to a fine off-white powder by bath sonication. The suspension was chilled in the refrigerator, then filtered to give 41.8 mg of crude product after drying.

$^1$H-NMR (D2O): 1.70 ppm (6 H, "t"=overlapped d of d, P—CH3s), 2.1–2.5 ppm (2 H, ms, H15), 3.5–3.7 ppm (ms, aminoethyl CH2s), , 4.4 ppm (1 H, m, H9), 5.2 ppm (1 H, d, 5.55 & 5.8 ppm (2 H, ds, H7 & H8), 6.7 & 6.8 ppm (2 H, d of d, H1 & H2), no MEM or BOC resonances. C18-HPLC on a 0.46×10 cm column in a linear gradient of 5–25% acetonitrile in 0.1% v/v TFA/water, 1.0 mL/min (0.66% B/min) showed a major peak at k'=3.17 and an impurity peak at k'=7.34. The product was purified by preparative HPLC on a 2.2×25 cm C18 column in the 5–25% gradient system at a flow rate of 16 mL/min. Pure fractions were recovered and lyophilized to give 21.3 mg. UV max=286 nm.

Example 9

6-O-Dimethylphosphinyl-N-(3-maleimido-propionamido)-Normorphine

The title compound was prepared as follows: 6-O-Dimethylphosphinyl-N-(2-aminoethyl)-Normorphine bisTFA, 9.8 mg (15.9 micromole), was dissolved in 0.75 mL DMF under argon. Triethylamine, 3.2 $\mu$L (23 micromole) was added followed by 3.6 mg (13.5 micromole) maleimidopropionic acid N-hydroxysuccinimide ester (MPS) in 0.25 mL DMF. The reaction was stirred at room temperature and monitored by C18-HPLC in the 5–25% gradient system described in example 8. Starting material at k'=3.28 was converted into product at k'=7.03. After 60 min, an additional 1.6 mg (6 micromole) of MPS and 1 $\mu$L (7.2 micromole) triethylamine was added to drive the reaction to completion. After 90 min., the reaction was placed in a −70° C. freezer until work-up.

The reaction mixture was worked up by diluting into 9 mL of 0.1% v/v TFA/water, filtering, and purifying the filtrate in two runs on a preparative C18-HPLC column (2.2×25 cm) using the 5–25% gradient system from example 8 at a flow rate of 16 mL/min. Pure fractions were pooled and lyophilized to give a total of 6.98 mg.

$^1$H-NMR (CD3OD): 1.7 & 1.8 ppm (6 H, "t"=d of d overlapped, P—CH3s), 2.1–2.5 ppm (2 H, ms, H15), 2.6 ppm (2 H, t, MPS CH2CO), 3.85 ppm (2 H, t, MPS CH2N), 4.45 ppm (1 H, m, H9), 5.2 ppm (1 H, d, H5), 5.6 & 5.85 ppm (2 H, d of d, H7 & H8), 6.75 & 6.85 ppm (2 H, d of d, H1 & H2), 6.9 ppm (2 H, s, maleimide H). UV max=286 nm.

Example 10

Preparation of carbamoyl analog protein conjugates

Conjugation of Normorphine-Carb-MPAE-MPA to the enzyme donor ED28 was performed as follows. A solution of desalted ED28 (1 mg) in phosphate buffer (833 $\mu$L, 100 mM, pH=7) was added with stirring to a solution of Normorphine-Carb-MPAE-UPA (380 $\mu$g) in DMF (204 $\mu$L). After standing at room temperature for 100 minutes TFA in water (1.4 mL, 0.1% v/v) was added and the mixture was desalted on a PD-10 pre-packed SEPHADEX G-25 ion exchange column (Pharmacia, Inc.) pre-equilibrated with 0.1% v/v TFA in water. TFA in water (1 mL, 0.1% v/v) was added to the eluate (3.5 mL) and the solution was injected in a 10 mL loop and purified by HPLC [C4 1×25 cm, 0 min, 100% A (0.1% v/v TFA); 0.1–20 min, 25–45% B (0.1% v/v TFA/McCN); flow rate=4 mL/min; 280 mn]. The purification afforded 3.07 mL of eluate. The yield was 579 $\mu$g (51%) as determined by UV absorbance at 280 nm ($\epsilon_{280}$=18,900 cm$^{-1}$M$^{-1}$). This solution was stored at −80° C. until further use.

Preparation of the carbamoyl analog immunogen (KLH-2-IT-CARB-MPAE-Normorphine) was performed as follows. 2-Iminothiolane (2-IT) (1.72 mg) was added to KLH (12.5 mg) in phosphate buffer (1.25 mL, 83 mM, pH=7.2, 0.9 M NaCl) with stirring. After 3 h phosphate buffer (1.25 mL, 100 mM, pH=7) was added to the mixture and it was desalted with a PD-10 pre-packed SEPHADEX G-25 ion exchange column (Pharmacia, Inc.) pre-equilibrated with phosphate buffer (100 mM, pH=7) to remove excess 2-IT. The eluate (3.5 mL) was added to Carbamoyl-MPAE-Normorphine (3.11 mg) in DMF (2 mL). After stirring for 1 h the mixture was dialyzed against phosphate buffer (800 mL, 10 mM, pH=7, 150 mM NaCl) and DMF (200 mL). After 12 hours the buffer was replaced. After an additional 12 hours this buffer was replaced with phosphate buffer (2 L, 10 mM, pH=7, 150 mM NaCl) which was again replaced after another 12 hours. Twelve hours after the last buffer replacement the immunogen solution (9 mL) was transferred to a vial and stored at −80° C. until used.

Example 11

Development of 6MAM Specific Monoclonal Antibodies

The antibodies were prepared by first administering the immunogens NM-DMP-MPAE-2IT-KLH or KLH-2IT- CARB-MPAE-NM or NM-MMP-MPAE-2IT-KLH to mice in a series of injections. Mice were bled after three immunizations, and again after two additional immunizations. The sera were assayed in 96-well plate version of a beta-galactosidase enzyme complementation assay (see Example 12). Data were as follows:

| Normorphine Immunogen | Average Titer (at 80% I Max) | Modulation with free 6MAM | Relative Morphine Cross-reactivity |
|---|---|---|---|
| Dimethylphosphonyl | | | |
| First Bleed | 1/709 | 7–11% range, 9% avg | 1–3% range, 1.75% avg |
| Second Bleed | 1/2728 | 14–37% range, 23% avg | 0.02–0.8% range, 0.3% avg |
| Carbamoyl | | | |
| First Bleed | 1/4838 | 14–33% range 21% avg | 0.1–0.8% range, 0.34% avg |
| Second Bleed | 1/12719 | 25–48% range 36% avg | 0.1–0.4% range, 0.3% avg |
| Monomethyl-phosphonyl | | | |
| First Bleed | 1/3525 | 0% | greater than 200% |
| Second Bleed | 1/15,506 | 13% (serum from only one mouse modulated) | not done |

These results indicate that all immunogens worked well to elicit a strong and specific (except in the case of the MMP immunogen) response. Mice from DMP or Carb groups were selected and hyperimmunized prior to fusion. The parental myeloma used for all fusions was P3X63-Ag8.653, purchased through the American Type Culture Collection (ATCC). The first fusion produced 71 clones which strongly bound the 6MAM conjugate in 96-well CEDIA® style enzyme complementation assay. Nineteen of these clones were retained on the basis of modulation at 1× cutoff. A second fusion was performed similarly, from which 50 initial 6MAM-binding positive clones were identified, 14 of which were retained. Culture supernates from retained lines were grown to provide antibody samples for instrumentation analysis via CEDIA®.

Chronology of events for antibodies raised using For NM-DMP-MPAE-2IT-KLH:

| First Immunization | Time 0 |
|---|---|
| Second Immunization | 2 weeks |
| Third Immunization | 4 weeks |
| Mice Bled | 6 weeks |
| Fourth Immunization | 35 weeks |
| Sera from first bleed titered | 64 weeks |
| Fifth Immunization | 67 weeks |
| Mice Bled | 69 weeks |
| Sera from second bleed titered | 69 weeks |
| First 6MAM Fusion performed | 89 weeks |
| First 6MAM Fusion screened | 90 weeks |

Chronology of events for antibodies raised using KLH-2IT-CARB-MPAE-NM

| First Immunization | Time 0 |
|---|---|
| Second Immunization | 2 weeks |
| Third Immunization | 5 weeks |
| Mice Bled | 7 weeks |
| Fourth Immunization | 60 weeks |
| Sera from first bleed titered | 59 weeks |
| Fifth Immunization | 62 weeks |
| Mice Bled | 63 weeks |
| Sera from second bleed titered | 63 weeks |
| Second 6MAM Fusion performed | 86 weeks |
| Second 6MAM Fusion screened | 87 weeks |

Example 12

Beta-galactosidase enzyme complementation assay for 6MAM

Enzyme acceptor (EA) Reagent was prepared by reconstituting a lyophilized EA reagent with EA reconstitution buffer (EARB) containing the 6-acetylmorphine antibody. The components and concentrations used are listed below.

| Component | F.W. or Stock | Conc. (*) |
|---|---|---|
| Lyophilized EA Reagent | | |
| Potassium Phosphate, dibasic | 174.18 g/mole | 10 mM |
| Potassium Phosphate, monobasic | 136.09 g/mole | 10 mM |
| Mannitol | 182.17 g/mole | 300 mM |
| Tween 20 | 10% | 0.01% |
| Sodium Azide | 65.01 g/mole | 9 mM |
| Glutathione | 307.30 g/mole | 0.5 mM |
| EA22 Protein | ~25–30% protein by weight | 1.713 g protein/L |
| EA Reconstitution Buffer | | |
| Potassium Phosphate, dibasic | 174.18 g/mole | 20 mM |
| Sodium Citrate | 294.1 g/mole | 120 mM |
| Sodium Chloride | 58.44 g/mole | 200 mM |
| EGTA | 380.35 g/mole | 12 mM |
| Magnesium Acetate | 214.46 g/mole | 12 mM |
| Fetal Bovine Serum | Neat | 0.5% |
| Sodium Azide | 65.01 g/mole | 20 mM |
| Goat Anti-Mouse IgG serum | Neat | 2% |
| 6MAM Ab | — | — |

Enzyme Donor (ED) Reagent was prepared as a liquid reagent with the components below.

| ED Reagent | | |
|---|---|---|
| Component | F.W. or Stock | Conc. |
| Potassium Phosphate, dibasic | 174.18 | 120 mM |
| Potassium Phosphate, monobasic | 136.09 | 30 mM |
| Sodium Chloride | 58.44 | 200 mM |
| EGTA | 380.35 | 12 mM |
| EDTA | 292.2 | 10 mM |
| fragmented BSA | ~38 mg/mL | 2 mg/mL |
| CPRG | ~120 mg/mL | 1.637 mg/mL |
| Sodium Azide | 65.01 | 20 mM |
| ED28-(MPAE-MAM)$_2$ | — | 2 nM |

Both reagents had a pH of 6.85.

The assay protocol was as follows: Sample was pipetted into a reaction cuvette and EA reagent, containing antibody, was added. The mixture was incubated at 37° C. for approximately 5 minutes and ED reagent containing substrate was subsequently added. The rate of substrate hydrolysis was then measured photometrically from four to five minutes after ED addition. The following table summarizes the assay protocol.

| Parameter | Set Point |
|---|---|
| Sample dispense | 10 μL |
| EA Reagent (R1) | 130 μL |
| Incubation | ~300 sec. |
| ED Reagent (R2) | 130 μL |
| Incubation | ~300 sec. |
| Read frame | 240–300 sec. after R2 |
| Wavelength | 660/570 (2°/1°) |

Figure 5A:
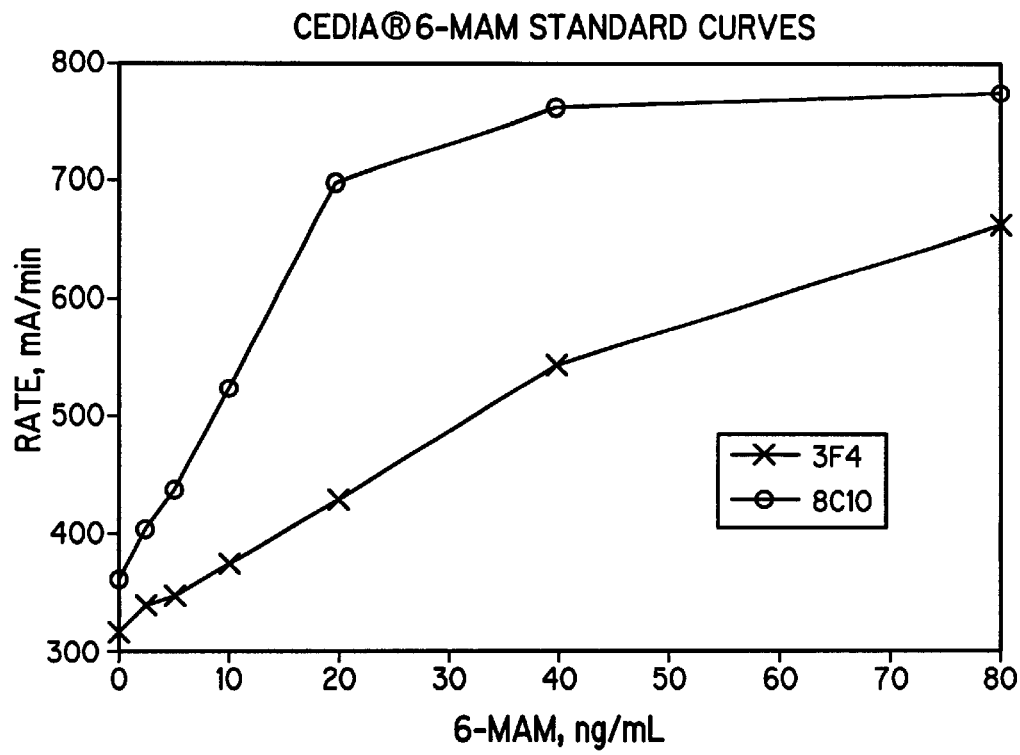
FIG. 5 is a two-panel graph relating to an enzyme complementation assay for 6MAM. 6MAM is conjugated through the normorphine nitrogen to an enzyme donor for beta-galactosidase. Antibody specific for 6MAM is raised using a dimethyl phosphonate analog conjugated to KLH. The assay mixture comprises the sample containing 6MAM, the enzyme donor conjugate, an enzyme acceptor, a beta-galactosidase substrate, and an antibody. Results of antibodies designated 3F4 (x) and 8C 10 (o) are shown. Upper panel shows enzyme rate (mA/min) as a function of 6MAM concentration in the sample. Lower panel shows the % modulation.
Figure 5B:
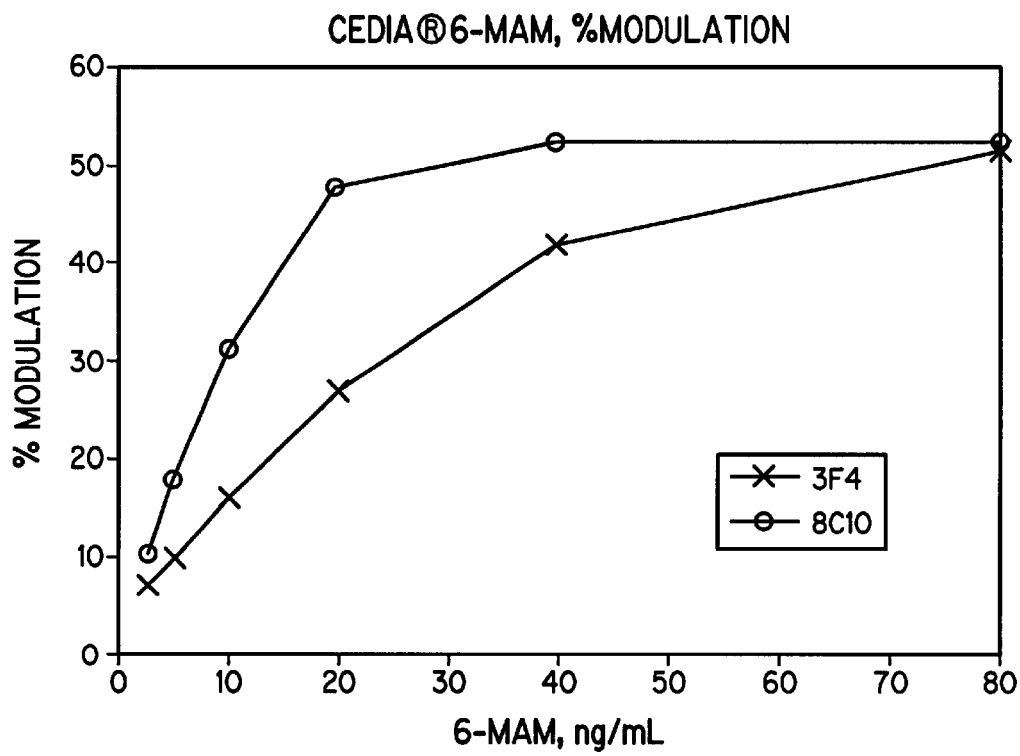

FIG. 5 shows representative standard curves using two different antibody clones (designated 3F4 and 8C10).

Cross reactivities to morphine, morphine metabolites, and codeine were evaluated for the 3F4 and 8C10 antibody clones. The results are listed below, and demonstrate both high sensitivity and high specificity.

Although the invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

All references, publications and patents mentioned herein are hereby incorporated by reference herein in their entirety.

MONOACETYL MORPHINE ANTIBODY SPECIFICITY

| Compound | Concentration ng/mL | Rate mAU/min | Apparent 6-MAM Dose ng/mL | Cross-Reactivity % |
|---|---|---|---|---|
| Antibody 3F4: Experiment 1 | | | | |
| Control | 0 | 600.4 | 0 | N/A |
| 6-Acetylmorphine | 2.5 | 629.7 | | |
| | 5 | 657.5 | | |
| | 10 | 700.2 | | |
| | 20 | 780.5 | | |
| | 40 | 865.8 | | |
| | 80 | 901.2 | | |
| Morphine | 4,000 | 617.6 | 1.5 | 0.04 |
| | 8,000 | 627.3 | 2.3 | 0.03 |
| | 75,000 | 827.3 | 31.0 | 0.04 |
| Codeine | 10,000 | 590.1 | <0.0 | <0.01 |
| | 100,000 | 600.1 | 0.0 | <0.01 |
| | 1,000,000 | 617.1 | 1.4 | <0.01 |
| Antibody 3F4: Experiment 2 | | | | |
| Control | 0 | 314.9 | 0 | N/A |
| 6-Acetylmorphine | 2.5 | 337.5 | | |
| | 5 | 347.7 | | |
| | 10 | 374.2 | | |
| | 20 | 430.0 | | |
| | 40 | 543.1 | | |
| | 80 | 662.3 | | |
| Morphine-3-glucuronide | 5,333 | 320.7 | 0.6 | 0.01 |
| | 10,666 | 320.3 | 0.6 | <0.01 |
| | 106,666 | 325.2 | 1.1 | <0.01 |
| Morphine-6-glucuronide | 5,333 | 324.3 | 1.0 | 0.02 |
| | 10,666 | 324.5 | 1.1 | 0.01 |
| | 106,666 | 339.0 | 2.9 | <0.01 |
| Antibody 8C10: Experiment 1 | | | | |
| Control | 0 | 475.7 | 0 | N/A |
| 6-Acetylmorphine | 2.5 | 519.2 | | |
| | 5 | 573.4 | | |
| | 10 | 670.9 | | |
| | 20 | 875.3 | | |
| | 40 | 947.0 | | |
| | 80 | 958.1 | | |
| Morphine | 4,000 | 656.8 | 9.3 | 0.23 |
| | 8,000 | 735.1 | 13.1 | 0.16 |
| | 75,000 | 927.2 | 34.5 | 0.05 |
| Codeine | 10,000 | 474.6 | <0.0 | <0.01 |
| | 100,000 | 481.7 | 0.3 | <0.01 |
| | 1,000,000 | 512.5 | 2.1 | <0.01 |
| Antibody 8C10: Experiment 2 | | | | |
| Control | 0 | 362.1 | 0 | N/A |
| 6-Acetylmorphine | 2.5 | 402.0 | | |
| | 5 | 439.1 | | |
| | 10 | 525.3 | | |
| | 20 | 697.4 | | |
| | 40 | 763.7 | | |
| | 80 | 774.0 | | |
| Morphine-3-glucuronide | 5,333 | 360.7 | <0.0 | <0.01 |
| | 10,666 | 364.9 | 0.2 | <0.01 |
| | 106,666 | 373.0 | 0.7 | <0.01 |
| Morphine-6-glucuronide | 5,333 | 373.0 | 0.7 | 0.01 |
| | 10,666 | 381.2 | 1.2 | 0.01 |
| | 106,666 | 462.4 | 6.4 | 0.01 |

What is claimed as the invention is:

1. A compound having the following structure:

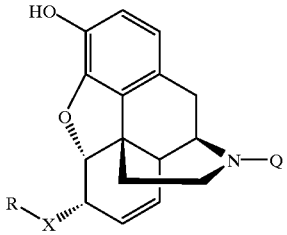

and its salts, wherein X is —O—, —S—, —NH— or —CH$_2$— and
wherein R is selected from the group consisting of:

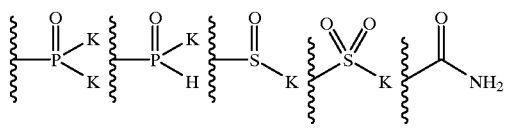

wherein K is —CH$_3$, —CF$_3$, —CHF$_2$, or —CH$_2$F; with
the proviso that when R is

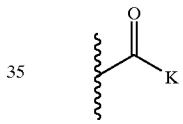

and K is —CH$_3$, X is not —O—; and

Q is —L$^1$—Z, where L$^1$ is a linker containing at least one carbon atom;

wherein Z is selected from the group consisting of the moieties
—NH$_2$,
—COOH,
—SH,

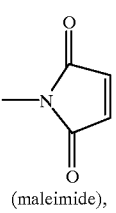

(maleimide),

—NH—C(=O)—L$^2$—M,

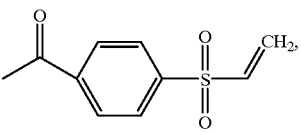

-continued

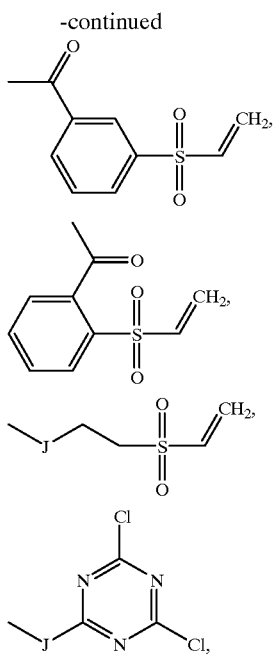

a moiety which reacts with a protein to form a covalent bond, or any combination or repetition of said moieties;

where $L^2$ is a linker containing at least one carbon atom;

where M is halide or maleimide; and wherein J is —O—, —S—, —NH— or —CH$_2$—.

2. The compound of claim 1, where X is —O— and R is selected from the group consisting of

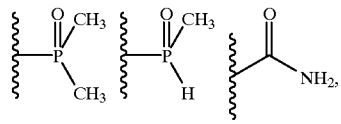

and where $L^1$ and $L^2$ are independently selected from the group consisting of C$_1$–C$_{20}$ hydrocarbon chains containing zero to ten heteroatoms selected from the group consisting of N, O, and S, and which contain at least as many carbon atoms as heteroatoms.

3. A compound of claim 1, covalently derivatized by attachment to a label either directly or through a linking group.

4. The compound of claim 3, wherein the label is selected from the group consisting of a moiety containing a radioisotope, a fluorescent group, a fluorescence quenching group, a phosphorescent group, a chemiluminescent group, a chromophoric group, an electrochemically active group, an electrochemiluminescent group, a group that undergoes a change in fluorescence, phosphorescence, chemiluminescence or electrochemical property upon binding, a peptide, a protein, a protein fragment, an immunogenic carrier, an enzyme, an enzyme inhibitor, an enzyme substrate, an enzyme cofactor, an enzyme prosthetic group, an enzyme donor, a solid particle, a gold particle, an antibody, and a nucleic acid.

5. A compound of claim 1 derivatized by covalent attachment to a solid surface or insoluble particulate.

6. A compound having the following structure:

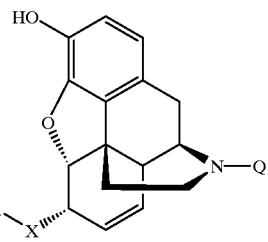

and its salts,
wherein X is —O—, —S—, —NH— or —CH$_2$— and wherein R is selected from the group consisting of:

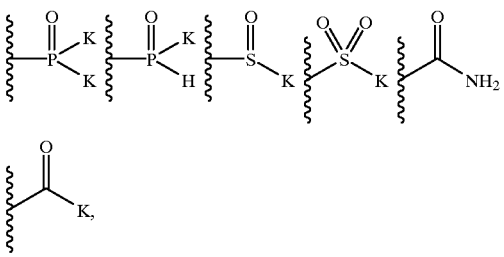

wherein K is —CH$_3$, —CF$_3$, —CHF$_2$, or —CH$_2$F; with the proviso that when R is

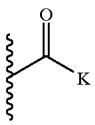

and K is —CH$_3$, X is not —O—; and

Q is —L$^1$—G, where L$^1$ is a linker containing at least one carbon atom, and G is selected from the group consisting of fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids.

7. A compound having the following structure:

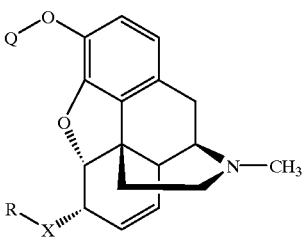

and its salts,
wherein X is —O—, —S—, —NH— or —CH$_2$— and wherein R is selected from the group consisting of:

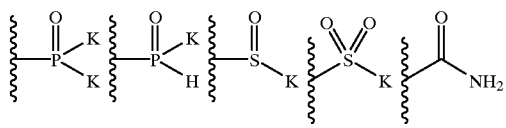

wherein K is —CH₃, —CF₃, —CHF₂, or —CH₂F; with the proviso that when R is

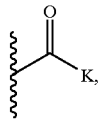

and K is —CH₃, X is not —O—;

Q is —L¹—Z, where L¹ is a linker containing at least one carbon atom;

wherein Z is selected from the group consisting of the moieties

—NH₂,
—COOH,
—SH,

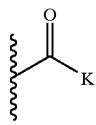
(maleimide),

—NH—C(=O)—L²—M,

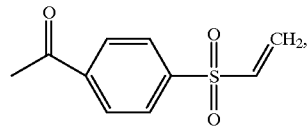

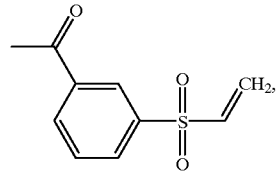

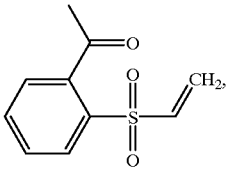

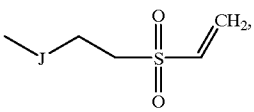

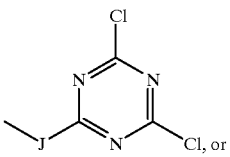

a moiety which reacts with a protein to form a covalent bond, or any combination or repetition of said moieties;

where L² is a linker containing at least one carbon atom; and wherein J is —O—, —S—, —NH— or —CH₂—.

8. A compound of claim 7 derivatized by covalent attachment to a label either directly or through a linking group.

9. The compound of claim 8, wherein the label is selected from the group consisting of a moiety containing a radioisotope, a fluorescent group, a fluorescence quenching group, a phosphorescent group, a chemiluminescent group, a chromophoric group, an electrochemically active group, an electrochemiluminescent group, a group that undergoes a change in fluorescence, phosphorescence, chemiluminescence or electrochemical property upon binding, a peptide, a protein, a protein fragment, an immunogenic carrier, an enzyme, an enzyme inhibitor, an enzyme substrate, an enzyme cofactor, an enzyme prosthetic group, an enzyme donor, a solid particle, a gold particle, an antibody, and a nucleic acid.

10. A compound of claim 7, derivatized by covalent attachment to a solid surface or insoluble particulate.

11. A compound of claim 1, derivatized by covalent attachment to a protein or peptide.

12. The compound of claim 11, wherein the protein or peptide is an enzyme.

13. The compound of claim 11, wherein the protein or peptide is an enzyme donor that complements with an enzyme acceptor to form an active enzyme complex.

14. The compound of claim 13, wherein the enzyme donor is ED28.

15. The compound of claim 11, wherein the protein or peptide is immunogenic.

* * * * *

UNITED STATES PATENT AND TRADEMARK OFFICE
CERTIFICATE OF CORRECTION

PATENT NO. : 6,262,265 B1
DATED : October 10, 2001
INVENTOR(S) : Rouhani et al.

It is certified that error appears in the above-identified patent and that said Letters Patent is hereby corrected as shown below:

Column 13,
Line 24, change "temperature of -30°C. for" to -- temperature of 0-30°C. for --.

Column 17,
Line 20, change "ml" to -- mL --.

Column 18,
Line 58, change "cliromophore" to -- chromophore --.

Column 27,
Lines 49-50, change "(1 H, d, 5.55" to -- (1 H, d, H5), 5.55 --.

Column 28,
Line 38, change "TFA/McCN);" to -- TFA/MeCN); --.
Line 38, change "280 mn]" to -- 280nm] --.

Column 30,
Line 65, the asterisk explanation is missing. Please add -- (*) Conc. indicates final concentration after reconstitution. --.

Column 31,
Line 33, change "240-300 sec. after R2" to -- ~240-300 sec. after R2 --.

Column 33,
Line 11, change "-galactosidase" to -- β-galactosidase --.

Signed and Sealed this

Fifth Day of March, 2002

*Attest:*

JAMES E. ROGAN
*Attesting Officer*     *Director of the United States Patent and Trademark Office*

SEQUENCE LISTING

<160> NUMBER OF SEQ ID NOS: 1

<210> SEQ ID NO 1
<211> LENGTH: 90
<212> TYPE: PRT
<213> ORGANISM: Artificial Sequence
<220> FEATURE:
<223> OTHER INFORMATION: 90 amino acid peptide containing residues 6-45
      of -galactosidase.

<400> SEQUENCE: 1

Met Asp Pro Ser Gly Asn Pro Tyr Gly Ile Asp Pro Thr Gln Ser Ser
 1               5                  10                  15

Pro Gly Asn Ile Asp Pro Cys Ala Ser Ser Asn Ser Leu Ala Val Val
                20                  25                  30

Leu Gln Arg Arg Asp Trp Glu Asn Pro Gly Val Thr Gln Leu Asn Arg
            35                  40                  45

Leu Ala Ala His Pro Pro Phe Ala Ser Trp Arg Asn Ser Glu Glu Ala
        50                  55                  60

Arg Thr Asp Cys Pro Ser Gln Gln Leu Ala Gln Pro Glu Trp Gly Leu
65                  70                  75                  80

Glu Ser Arg Ser Ala Gly Met Pro Leu Glu
                85                  90